(12) United States Patent
Bolanos et al.

(10) Patent No.: US 9,642,608 B2
(45) Date of Patent: May 9, 2017

(54) GELS HAVING PERMANENT TACK FREE COATINGS AND METHOD OF MANUFACTURE

(71) Applicant: Applied Medical Resources Corporation, Rancho Santa Margarita, CA (US)

(72) Inventors: Eduardo Bolanos, Rancho Santa Margarita, CA (US); Dennis Bui, Rancho Santa Margarita, CA (US); Boun Pravong, Rancho Santa Margarita, CA (US); Carlos Pinel, Rancho Santa Margarita, CA (US); Sam Chehayeb, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 0 days.

(21) Appl. No.: 14/801,553

(22) Filed: Jul. 16, 2015

(65) Prior Publication Data

US 2016/0015425 A1    Jan. 21, 2016

Related U.S. Application Data

(60) Provisional application No. 62/026,317, filed on Jul. 18, 2014.

(51) Int. Cl.
*A61B 17/34* (2006.01)
*B29C 33/56* (2006.01)
(Continued)

(52) U.S. Cl.
CPC ...... *A61B 17/0293* (2013.01); *A61B 17/3423* (2013.01); *A61B 17/3462* (2013.01);
(Continued)

(58) Field of Classification Search
CPC . A61B 17/3498; A61B 17/0293; B29C 33/56; B29C 45/1679; B29C 45/73; B29K 2025/08
(Continued)

(56) References Cited

U.S. PATENT DOCUMENTS 558,364 A    4/1896    Doolittle
1,157,202 A    10/1915    Bates et al.
(Continued)

FOREIGN PATENT DOCUMENTS

DE    26 05 148 A1    8/1977
DE    33 36 279 C2    1/1986
(Continued)

OTHER PUBLICATIONS

U.S. Appl. No. 10/381,220, filed Mar. 20, 2003; Title: Surgical Access Apparatus and Method, now USPN 7,473,221 issued Jan. 6, 2009.
(Continued)

*Primary Examiner* — Pedro Philogene
*Assistant Examiner* — David C Comstock
(74) *Attorney, Agent, or Firm* — Cynthia A. Bonner

(57) ABSTRACT

The present invention is directed to tack-free gels and to methods for manufacturing a tack-free gel pad, in which a discontinuous layer of fluorinated ultrahigh molecular weight polyethylene is permanently bonded to the gel pad to provide a tack-free coating. The gel pad may be incorporated into a gel cap to provide a surgical access device having a tack-free surface.

16 Claims, 11 Drawing Sheets

(51) Int. Cl.
  *A61B 17/02* (2006.01)
  *B29C 45/16* (2006.01)
  *B29C 45/73* (2006.01)
  *A61L 31/14* (2006.01)
  *B29C 33/62* (2006.01)
  *A61L 31/04* (2006.01)
  *B29K 25/00* (2006.01)
  *B29L 9/00* (2006.01)
  *B29C 39/02* (2006.01)

(52) U.S. Cl.
  CPC ........... *A61L 31/048* (2013.01); *A61L 31/145* (2013.01); *B29C 33/62* (2013.01); *B29C 45/1679* (2013.01); *B29C 45/73* (2013.01); *A61B 2017/3492* (2013.01); *B29C 33/56* (2013.01); *B29C 39/02* (2013.01); *B29K 2025/08* (2013.01); *B29K 2995/0037* (2013.01); *B29L 2009/005* (2013.01)

(58) Field of Classification Search
  USPC .......... 600/201–246; 606/119; 128/846, 856; 249/114.1, 115
  See application file for complete search history.

(56) References Cited

U.S. PATENT DOCUMENTS

| | | |
|---|---|---|
| 1,598,284 A | 8/1926 | Kinney |
| 1,690,995 A | 11/1928 | Pratt |
| 1,180,466 A | 6/1931 | Deutsch |
| 1,810,466 A | 6/1931 | Deutsch |
| 2,219,564 A | 10/1940 | Reyniers |
| 2,305,289 A | 12/1942 | Coburg |
| 2,478,586 A | 8/1949 | Krapp |
| 2,669,991 A | 2/1954 | Curutchet |
| 2,695,608 A | 11/1954 | Gibbon |
| 2,812,758 A | 11/1957 | Blumenschein |
| 2,835,253 A | 5/1958 | Borgeson |
| 2,853,075 A | 9/1958 | Hoffman et al. |
| 3,039,468 A | 6/1962 | Price |
| 3,057,350 A | 10/1962 | Cowley |
| 3,111,943 A | 11/1963 | Orndorff |
| 3,127,457 A * | 3/1964 | Di Pinto ............... B29C 33/62 249/114.1 |
| 3,195,934 A | 7/1965 | Parrish |
| 3,244,169 A | 4/1966 | Baxter |
| 3,253,594 A | 5/1966 | Matthews et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,416,520 A | 12/1968 | Creager, Jr. |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,656,485 A | 4/1972 | Robertson |
| 3,685,786 A | 8/1972 | Woodson |
| 3,717,151 A | 2/1973 | Collett |
| 3,717,883 A | 2/1973 | Mosher |
| 3,729,006 A | 4/1973 | Wilder et al. |
| 3,729,027 A | 4/1973 | Bare |
| 3,782,370 A | 1/1974 | McDonald |
| 3,797,478 A | 3/1974 | Walsh et al. |
| 3,799,166 A | 3/1974 | Marsan |
| 3,807,393 A | 4/1974 | McDonald |
| 3,828,764 A | 8/1974 | Jones |
| 3,831,583 A | 8/1974 | Edmunds et al. |
| 3,841,332 A | 10/1974 | Treacle |
| 3,850,172 A | 11/1974 | Cazalis |
| 3,853,126 A | 12/1974 | Schulte |
| 3,853,127 A | 12/1974 | Spademan |
| 3,856,021 A | 12/1974 | McIntosh |
| 3,860,274 A | 1/1975 | Ledstrom et al. |
| 3,861,416 A | 1/1975 | Wichterle |
| 3,907,389 A | 9/1975 | Cox et al. |
| 3,915,171 A | 10/1975 | Shermeta |
| 3,965,890 A | 6/1976 | Gauthier |
| 3,970,089 A | 7/1976 | Saice |
| 3,996,623 A | 12/1976 | Kaster |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,043,328 A | 8/1977 | Cawood, Jr. et al. |
| 4,069,913 A | 1/1978 | Harrigan |
| 4,083,370 A | 4/1978 | Taylor |
| 4,096,853 A | 6/1978 | Weigand |
| 4,112,932 A | 9/1978 | Chiulli |
| 4,117,847 A | 10/1978 | Clayton |
| 4,130,113 A | 12/1978 | Graham |
| 4,177,814 A | 12/1979 | Knepshield et al. |
| 4,183,357 A | 1/1980 | Bentley et al. |
| 4,187,849 A | 2/1980 | Stim |
| 4,188,945 A | 2/1980 | Wenander |
| 4,217,664 A | 8/1980 | Faso |
| 4,222,126 A | 9/1980 | Boretos et al. |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,254,973 A | 3/1981 | Benjamin |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lerman |
| 4,367,728 A | 1/1983 | Mutke |
| 4,369,284 A | 1/1983 | Chen |
| 4,399,816 A | 8/1983 | Spangler |
| 4,402,683 A | 9/1983 | Kopman |
| 4,411,659 A | 10/1983 | Jensen et al. |
| 4,421,296 A | 12/1983 | Stephens |
| 4,424,833 A | 1/1984 | Spector et al. |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,454,873 A | 6/1984 | Laufenberg et al. |
| 4,473,067 A | 9/1984 | Schiff |
| 4,475,548 A | 10/1984 | Muto |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,555,242 A | 11/1985 | Saudagar |
| 4,556,996 A | 12/1985 | Wallace |
| 4,601,710 A | 7/1986 | Moll |
| 4,610,665 A | 9/1986 | Matsumoto et al. |
| 4,626,245 A | 12/1986 | Weinstein |
| 4,634,424 A | 1/1987 | O'Boyle |
| 4,634,432 A | 1/1987 | Kocak |
| 4,644,951 A | 2/1987 | Bays |
| 4,649,904 A | 3/1987 | Krauter |
| 4,653,476 A | 3/1987 | Bonnet |
| 4,654,030 A | 3/1987 | Moll et al. |
| 4,655,752 A | 4/1987 | Honkanen et al. |
| 4,673,393 A | 6/1987 | Suzuki et al. |
| 4,673,394 A | 6/1987 | Fenton |
| 4,691,942 A | 9/1987 | Ford |
| 4,714,749 A | 12/1987 | Hughes et al. |
| 4,738,666 A | 4/1988 | Fuqua |
| 4,755,170 A | 7/1988 | Golden |
| 4,760,933 A | 8/1988 | Christner et al. |
| 4,776,843 A | 10/1988 | Martinez et al. |
| 4,777,943 A | 10/1988 | Chvapil |
| 4,784,646 A | 11/1988 | Feingold |
| 4,796,629 A | 1/1989 | Grayzel |
| 4,798,594 A | 1/1989 | Hillstead |

(56) References Cited

U.S. PATENT DOCUMENTS

| | | |
|---|---|---|
| 4,802,694 A | 2/1989 | Vargo |
| 4,808,168 A | 2/1989 | Warring |
| 4,809,679 A | 3/1989 | Shimonaka et al. |
| 4,828,554 A | 5/1989 | Griffin |
| 4,842,931 A | 6/1989 | Zook |
| 4,848,575 A | 7/1989 | Nakamura et al. |
| 4,856,502 A | 8/1989 | Ersfeld et al. |
| 4,863,430 A | 9/1989 | Klyce et al. |
| 4,863,438 A | 9/1989 | Gauderer et al. |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,911,974 A | 3/1990 | Shimizu et al. |
| 4,915,132 A | 4/1990 | Hodge et al. |
| 4,926,882 A | 5/1990 | Lawrence |
| 4,929,235 A | 5/1990 | Merry et al. |
| 4,944,732 A | 7/1990 | Russo |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,000,745 A | 3/1991 | Guest et al. |
| 5,009,224 A | 4/1991 | Cole |
| 5,015,228 A | 5/1991 | Columbus et al. |
| 5,019,101 A | 5/1991 | Purkait et al. |
| 5,026,366 A | 6/1991 | Leckrone |
| 5,037,379 A | 8/1991 | Clayman et al. |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,073,169 A | 12/1991 | Raiken |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima et al. |
| 5,104,389 A | 4/1992 | Deem |
| 5,125,396 A | 6/1992 | Ray |
| 5,125,897 A | 6/1992 | Quinn et al. |
| 5,127,626 A | 7/1992 | Hilal et al. |
| 5,129,885 A | 7/1992 | Green et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,167,637 A | 12/1992 | Okada et al. |
| 5,176,648 A | 1/1993 | Holmes et al. |
| 5,176,662 A | 1/1993 | Bartholomew et al. |
| 5,176,697 A | 1/1993 | Hasson et al. |
| 5,178,162 A | 1/1993 | Bose |
| 5,180,365 A | 1/1993 | Ensminger et al. |
| 5,183,471 A | 2/1993 | Wilk |
| 5,188,595 A | 2/1993 | Jacobi |
| 5,188,607 A | 2/1993 | Wu |
| 5,192,301 A | 3/1993 | Kamiya et al. |
| 5,197,955 A | 3/1993 | Stephens et al. |
| 5,207,656 A | 5/1993 | Kranys |
| 5,209,737 A | 5/1993 | Ritchart et al. |
| 5,211,370 A | 5/1993 | Powers |
| 5,211,633 A | 5/1993 | Stouder, Jr. |
| 5,213,114 A | 5/1993 | Bailey, Jr. |
| 5,226,890 A | 7/1993 | Ianniruberto et al. |
| 5,234,455 A | 8/1993 | Mulhollan |
| 5,241,968 A | 9/1993 | Slater |
| 5,242,400 A | 9/1993 | Blake, III et al. |
| 5,242,409 A | 9/1993 | Buelna |
| 5,242,412 A | 9/1993 | Blake, III |
| 5,242,415 A | 9/1993 | Kantrowitz et al. |
| 5,248,304 A | 9/1993 | Vigdorchik et al. |
| 5,256,150 A | 10/1993 | Quiachon et al. |
| 5,257,973 A | 11/1993 | Villasuso |
| 5,257,975 A | 11/1993 | Foshee |
| 5,259,366 A | 11/1993 | Reydel et al. |
| 5,261,883 A | 11/1993 | Hood et al. |
| 5,262,468 A | 11/1993 | Chen |
| 5,263,922 A | 11/1993 | Sova et al. |
| 5,269,763 A | 12/1993 | Boehmer et al. |
| 5,269,772 A | 12/1993 | Wilk |
| 5,273,449 A | 12/1993 | Mattis et al. |
| 5,273,545 A | 12/1993 | Hunt et al. |
| D343,236 S | 1/1994 | Quigley et al. |
| 5,279,575 A | 1/1994 | Sugarbaker |
| 5,290,310 A | 3/1994 | Makower et al. |
| D346,022 S | 4/1994 | Quigley et al. |
| 5,299,582 A | 4/1994 | Potts |
| 5,300,034 A | 4/1994 | Behnke |
| 5,300,035 A | 4/1994 | Clement |
| 5,300,036 A | 4/1994 | Mueller et al. |
| 5,308,336 A | 5/1994 | Hart et al. |
| 5,309,896 A | 5/1994 | Moll et al. |
| 5,312,391 A | 5/1994 | Wilk |
| 5,314,417 A | 5/1994 | Stephens et al. |
| 5,316,541 A | 5/1994 | Fischer |
| 5,320,611 A | 6/1994 | Bonutti et al. |
| 5,330,437 A | 7/1994 | Durman |
| 5,330,486 A | 7/1994 | Wilk |
| 5,330,497 A | 7/1994 | Freitas et al. |
| 5,331,975 A | 7/1994 | Bonutti |
| 5,334,143 A | 8/1994 | Carroll |
| 5,334,646 A | 8/1994 | Chen |
| 5,336,192 A | 8/1994 | Palestrant |
| 5,336,708 A | 8/1994 | Chen |
| 5,338,313 A | 8/1994 | Mollenauer et al. |
| 5,342,315 A | 8/1994 | Rowe et al. |
| 5,342,385 A | 8/1994 | Norelli et al. |
| 5,350,364 A | 9/1994 | Stephens et al. |
| 5,353,786 A | 10/1994 | Wilk |
| 5,354,280 A | 10/1994 | Haber et al. |
| 5,360,417 A | 11/1994 | Gravener et al. |
| 5,364,345 A | 11/1994 | Lowery et al. |
| 5,364,372 A | 11/1994 | Danks et al. |
| 5,366,446 A | 11/1994 | Tal et al. |
| 5,366,478 A | 11/1994 | Brinkerhoff et al. |
| 5,368,545 A | 11/1994 | Schaller et al. |
| 5,375,588 A | 12/1994 | Yoon |
| 5,380,288 A | 1/1995 | Hart et al. |
| 5,383,861 A | 1/1995 | Hempel et al. |
| 5,385,552 A | 1/1995 | Haber et al. |
| 5,385,553 A | 1/1995 | Hart et al. |
| 5,385,560 A | 1/1995 | Wulf |
| 5,389,080 A | 2/1995 | Yoon |
| 5,389,081 A | 2/1995 | Castro |
| 5,391,153 A | 2/1995 | Haber et al. |
| 5,391,156 A | 2/1995 | Hildwein et al. |
| 5,395,367 A | 3/1995 | Wilk |
| 5,403,264 A | 4/1995 | Wohlers et al. |
| 5,403,336 A | 4/1995 | Kieturakis et al. |
| 5,407,433 A | 4/1995 | Loomas |
| 5,411,483 A | 5/1995 | Loomas |
| 5,413,571 A | 5/1995 | Katsaros et al. |
| 5,423,848 A | 6/1995 | Washizuka et al. |
| 5,429,609 A | 7/1995 | Yoon |
| 5,431,676 A | 7/1995 | Dubrul et al. |
| 5,437,683 A | 8/1995 | Neumann et al. |
| 5,439,455 A | 8/1995 | Kieturakis et al. |
| 5,441,486 A | 8/1995 | Yoon |
| 5,443,452 A | 8/1995 | Hart et al. |
| 5,456,284 A | 10/1995 | Ryan et al. |
| 5,460,170 A | 10/1995 | Hammerslag |
| 5,460,616 A | 10/1995 | Weinstein et al. |
| 5,468,248 A | 11/1995 | Chin et al. |
| 5,476,475 A | 12/1995 | Gadberry |
| 5,480,410 A | 1/1996 | Cuschieri et al. |
| 5,486,426 A | 1/1996 | McGee et al. |
| 5,490,843 A | 2/1996 | Hildwein et al. |
| 5,492,304 A | 2/1996 | Smith et al. |
| 5,496,280 A | 3/1996 | Vandenbroek et al. |
| 5,503,112 A | 4/1996 | Luhman et al. |
| 5,507,758 A | 4/1996 | Thomason et al. |

(56) References Cited

U.S. PATENT DOCUMENTS

| | | |
|---|---|---|
| 5,508,334 A | 4/1996 | Chen |
| 5,511,564 A | 4/1996 | Wilk |
| 5,514,109 A | 5/1996 | Mollenauer et al. |
| 5,514,133 A | 5/1996 | Golub et al. |
| 5,514,153 A | 5/1996 | Bonutti |
| 5,518,278 A | 5/1996 | Sampson |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,531,758 A | 7/1996 | Uschold et al. |
| 5,538,509 A | 7/1996 | Dunlap et al. |
| 5,540,648 A | 7/1996 | Yoon |
| 5,540,711 A | 7/1996 | Kieturakis et al. |
| 5,545,150 A | 8/1996 | Danks et al. |
| 5,545,179 A | 8/1996 | Williamson, IV |
| 5,549,563 A | 8/1996 | Kronner |
| 5,549,637 A | 8/1996 | Crainich |
| 5,554,124 A | 9/1996 | Alvarado |
| 5,562,632 A | 10/1996 | Davila et al. |
| 5,562,677 A | 10/1996 | Hildwein et al. |
| 5,562,688 A | 10/1996 | Riza |
| 5,571,115 A | 11/1996 | Nicholas |
| 5,571,137 A | 11/1996 | Marlow et al. |
| 5,575,799 A | 11/1996 | Bolanos et al. |
| 5,577,993 A | 11/1996 | Zhu et al. |
| 5,578,048 A | 11/1996 | Pasqualucci et al. |
| 5,580,344 A | 12/1996 | Hasson |
| 5,584,850 A | 12/1996 | Hart et al. |
| 5,601,579 A | 2/1997 | Semertzides |
| 5,601,581 A | 2/1997 | Fogarty et al. |
| 5,603,702 A | 2/1997 | Smith et al. |
| 5,607,443 A | 3/1997 | Kieturakis et al. |
| 5,620,415 A | 4/1997 | Lucey et al. |
| 5,620,420 A | 4/1997 | Kriesel |
| 5,628,732 A | 5/1997 | Antoon, Jr. et al. |
| 5,632,284 A | 5/1997 | Graether |
| 5,632,979 A | 5/1997 | Goldberg et al. |
| 5,634,911 A | 6/1997 | Hermann et al. |
| 5,634,936 A | 6/1997 | Linden et al. |
| 5,634,937 A | 6/1997 | Mollenauer et al. |
| 5,636,645 A | 6/1997 | Ou |
| 5,640,977 A | 6/1997 | Leahy et al. |
| 5,643,301 A | 7/1997 | Mollenauer |
| 5,649,550 A | 7/1997 | Crook |
| 5,651,771 A | 7/1997 | Tangherlini et al. |
| 5,653,705 A | 8/1997 | de la Torre et al. |
| 5,657,963 A | 8/1997 | Hinchliffe et al. |
| 5,658,272 A | 8/1997 | Hasson |
| 5,658,306 A | 8/1997 | Kieturakis et al. |
| 5,662,615 A | 9/1997 | Blake, III |
| 5,672,168 A | 9/1997 | de la Torre et al. |
| 5,681,341 A | 10/1997 | Lunsford et al. |
| 5,683,378 A | 11/1997 | Christy |
| 5,685,854 A | 11/1997 | Green et al. |
| 5,685,857 A | 11/1997 | Negus et al. |
| 5,697,914 A | 12/1997 | Brimhall |
| 5,707,703 A | 1/1998 | Rothrum et al. |
| 5,709,664 A | 1/1998 | Vandenbroek et al. |
| 5,713,858 A | 2/1998 | Heruth et al. |
| 5,713,869 A | 2/1998 | Morejon |
| 5,720,730 A | 2/1998 | Blake, III |
| 5,725,536 A | 3/1998 | Oberlin et al. |
| 5,728,103 A | 3/1998 | Picha et al. |
| 5,730,748 A | 3/1998 | Fogarty et al. |
| 5,735,791 A | 4/1998 | Alexander et al. |
| 5,738,628 A | 4/1998 | Sierocuk et al. |
| 5,741,234 A | 4/1998 | Aboul-Hosn |
| 5,741,298 A | 4/1998 | MacLeod |
| 5,743,884 A | 4/1998 | Hasson et al. |
| 5,749,882 A | 5/1998 | Hart et al. |
| 5,755,660 A | 5/1998 | Tyagi |
| 5,760,117 A | 6/1998 | Chen |
| 5,769,783 A | 6/1998 | Fowler |
| 5,782,812 A | 7/1998 | Hart et al. |
| 5,782,817 A | 7/1998 | Franzel et al. |
| 5,782,859 A | 7/1998 | Nicholas et al. |
| 5,788,676 A | 8/1998 | Yoon |
| 5,792,119 A | 8/1998 | Marx |
| 5,795,290 A | 8/1998 | Bridges |
| 5,803,919 A | 9/1998 | Hart et al. |
| 5,803,921 A | 9/1998 | Bonadio |
| 5,803,923 A | 9/1998 | Singh-Derewa et al. |
| 5,807,350 A | 9/1998 | Diaz |
| 5,810,712 A | 9/1998 | Dunn |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom et al. |
| 5,819,375 A | 10/1998 | Kastner |
| 5,820,555 A | 10/1998 | Watkins, III et al. |
| 5,820,600 A | 10/1998 | Carlson et al. |
| 5,830,191 A | 11/1998 | Hildwein et al. |
| 5,832,925 A | 11/1998 | Rothrum |
| 5,836,871 A | 11/1998 | Wallace et al. |
| 5,841,298 A | 11/1998 | Huang |
| 5,842,971 A | 12/1998 | Yoon |
| 5,848,992 A | 12/1998 | Hart et al. |
| 5,853,395 A | 12/1998 | Crook et al. |
| 5,853,417 A | 12/1998 | Fogarty et al. |
| 5,857,461 A | 1/1999 | Levitsky et al. |
| 5,860,995 A | 1/1999 | Berkelaar |
| 5,865,728 A | 2/1999 | Moll et al. |
| 5,865,729 A | 2/1999 | Meehan et al. |
| 5,865,807 A | 2/1999 | Blake, III |
| 5,865,817 A | 2/1999 | Moenning et al. |
| 5,871,474 A | 2/1999 | Hermann et al. |
| 5,876,413 A | 3/1999 | Fogarty et al. |
| 5,879,368 A | 3/1999 | Hoskin et al. |
| 5,882,344 A | 3/1999 | Stouder, Jr. |
| 5,884,639 A | 3/1999 | Chen |
| 5,894,843 A | 4/1999 | Benetti et al. |
| 5,895,377 A | 4/1999 | Smith et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,913,847 A | 6/1999 | Yoon |
| 5,916,198 A | 6/1999 | Dillow |
| 5,916,232 A | 6/1999 | Hart |
| 5,919,476 A | 7/1999 | Fischer et al. |
| 5,931,832 A | 8/1999 | Jensen |
| 5,947,922 A | 9/1999 | MacLeod |
| 5,951,467 A | 9/1999 | Picha et al. |
| 5,951,588 A | 9/1999 | Moenning |
| 5,957,888 A | 9/1999 | Hinchliffe |
| 5,957,913 A | 9/1999 | de la Torre et al. |
| 5,962,572 A | 10/1999 | Chen |
| 5,964,781 A | 10/1999 | Mollenauer et al. |
| 5,976,174 A | 11/1999 | Ruiz |
| 5,989,232 A | 11/1999 | Yoon |
| 5,989,233 A | 11/1999 | Yoon |
| 5,989,266 A | 11/1999 | Foster |
| 5,993,471 A | 11/1999 | Riza et al. |
| 5,993,485 A | 11/1999 | Beckers |
| 5,994,450 A | 11/1999 | Pearce |
| 5,997,515 A | 12/1999 | de la Torre et al. |
| 6,004,303 A | 12/1999 | Peterson |
| 6,010,494 A | 1/2000 | Schafer et al. |
| 6,017,355 A | 1/2000 | Hessel et al. |
| 6,018,094 A | 1/2000 | Fox |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,035,559 A | 3/2000 | Freed et al. |
| 6,042,573 A | 3/2000 | Lucey |
| 6,045,535 A | 4/2000 | Ben Nun |
| 6,048,309 A | 4/2000 | Flom et al. |
| 6,050,871 A | 4/2000 | Chen |
| 6,053,934 A | 4/2000 | Andrews et al. |
| 6,059,816 A | 5/2000 | Moenning |
| 6,066,117 A | 5/2000 | Fox et al. |

(56) References Cited

U.S. PATENT DOCUMENTS

| | | |
|---|---|---|
| 6,068,639 A | 5/2000 | Fogarty et al. |
| 6,076,560 A | 6/2000 | Stahle et al. |
| 6,077,288 A | 6/2000 | Shimomura |
| 6,086,603 A | 7/2000 | Termin et al. |
| 6,090,043 A | 7/2000 | Austin et al. |
| 6,099,506 A | 8/2000 | Macoviak et al. |
| 6,110,154 A | 8/2000 | Shimomura et al. |
| 6,123,689 A | 9/2000 | To et al. |
| 6,142,935 A | 11/2000 | Flom et al. |
| 6,142,936 A | 11/2000 | Beane et al. |
| 6,149,642 A | 11/2000 | Gerhart et al. |
| 6,150,608 A | 11/2000 | Wambeke et al. |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,197,002 B1 | 3/2001 | Peterson |
| 6,217,555 B1 | 4/2001 | Hart et al. |
| 6,217,590 B1 | 4/2001 | Levinson |
| 6,224,612 B1 | 5/2001 | Bates et al. |
| 6,228,063 B1 | 5/2001 | Aboul-Hosn |
| 6,238,373 B1 | 5/2001 | de la Torre et al. |
| 6,241,768 B1 | 6/2001 | Agarwal et al. |
| 6,254,533 B1 | 7/2001 | Fadem et al. |
| 6,254,534 B1 | 7/2001 | Butler et al. |
| 6,258,065 B1 | 7/2001 | Dennis et al. |
| 6,264,604 B1 | 7/2001 | Kieturakis et al. |
| 6,267,751 B1 | 7/2001 | Mangosong |
| 6,276,661 B1 | 8/2001 | Laird |
| 6,287,280 B1 | 9/2001 | Lampropoulos et al. |
| 6,315,770 B1 | 11/2001 | de la Torre et al. |
| 6,319,246 B1 | 11/2001 | de la Torre et al. |
| 6,322,541 B2 | 11/2001 | West |
| 6,325,384 B1 | 12/2001 | Berry, Sr. et al. |
| 6,346,074 B1 | 2/2002 | Roth |
| 6,371,968 B1 | 4/2002 | Kogasaka et al. |
| 6,382,211 B1 | 5/2002 | Crook |
| 6,383,162 B1 | 5/2002 | Sugarbaker |
| 6,391,043 B1 | 5/2002 | Moll et al. |
| 6,413,244 B1 | 7/2002 | Bestetti et al. |
| 6,413,458 B1 | 7/2002 | Pearce |
| 6,420,475 B1 | 7/2002 | Chen |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,482,181 B1 | 11/2002 | Racenet et al. |
| 6,485,435 B1 | 11/2002 | Bakal |
| 6,485,467 B1 | 11/2002 | Crook et al. |
| 6,488,620 B1 | 12/2002 | Segermark et al. |
| 6,488,692 B1 | 12/2002 | Spence et al. |
| 6,494,893 B2 | 12/2002 | Dubrul et al. |
| 6,527,787 B1 | 3/2003 | Fogarty et al. |
| 6,533,734 B1 | 3/2003 | Corley, III et al. |
| 6,551,270 B1 | 4/2003 | Bimbo et al. |
| 6,551,276 B1 | 4/2003 | Mann et al. |
| 6,551,344 B2 | 4/2003 | Thill |
| 6,552,109 B1 | 4/2003 | Chen |
| 6,554,793 B1 | 4/2003 | Pauker et al. |
| 6,558,371 B2 | 5/2003 | Dorn |
| 6,569,120 B1 | 5/2003 | Green |
| 6,578,577 B2 | 6/2003 | Bonadio et al. |
| 6,579,281 B2 | 6/2003 | Palmer et al. |
| 6,582,364 B2 | 6/2003 | Butler et al. |
| 6,589,167 B1 | 7/2003 | Shimomura et al. |
| 6,589,211 B1 | 7/2003 | MacLeod |
| 6,607,504 B2 | 8/2003 | Haarala et al. |
| 6,613,952 B2 | 9/2003 | Rambo |
| 6,623,426 B2 | 9/2003 | Bonadio et al. |
| 6,627,275 B1 | 9/2003 | Chen |
| 6,663,598 B1 | 12/2003 | Carrillo et al. |
| 6,669,674 B1 | 12/2003 | Macoviak et al. |
| 6,676,639 B1 | 1/2004 | Ternström |
| 6,692,817 B1 * | 2/2004 | Silva .............. B05D 5/083 249/114.1 |
| 6,702,787 B2 | 3/2004 | Racenet et al. |
| 6,705,989 B2 | 3/2004 | Cuschieri et al. |
| 6,706,050 B1 | 3/2004 | Giannadakis |
| 6,714,298 B2 | 3/2004 | Ryer |
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,793,621 B2 | 9/2004 | Butler et al. |
| 6,794,440 B2 | 9/2004 | Chen |
| 6,796,940 B2 | 9/2004 | Bonadio et al. |
| 6,797,765 B2 | 9/2004 | Pearce |
| 6,800,084 B2 | 10/2004 | Davison et al. |
| 6,811,546 B1 | 11/2004 | Callas et al. |
| 6,814,078 B2 | 11/2004 | Crook |
| 6,814,700 B1 | 11/2004 | Mueller et al. |
| 6,817,974 B2 | 11/2004 | Cooper et al. |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,863,674 B2 | 3/2005 | Kasahara et al. |
| 6,866,861 B1 | 3/2005 | Luhman |
| 6,867,253 B1 | 3/2005 | Chen |
| 6,869,393 B2 | 3/2005 | Butler |
| 6,878,110 B2 | 4/2005 | Yang et al. |
| 6,884,253 B1 | 4/2005 | McFarlane |
| 6,890,295 B2 | 5/2005 | Michels et al. |
| 6,895,965 B2 | 5/2005 | Scarberry et al. |
| 6,902,541 B2 | 6/2005 | McNally et al. |
| 6,902,569 B2 | 6/2005 | Parmer et al. |
| 6,908,430 B2 | 6/2005 | Caldwell et al. |
| 6,909,220 B2 | 6/2005 | Chen |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,936,037 B2 | 8/2005 | Bubb et al. |
| 6,939,296 B2 | 9/2005 | Ewers et al. |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,979,324 B2 | 12/2005 | Bybordi et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,304 B2 | 6/2006 | Bacher et al. |
| 7,056,321 B2 | 6/2006 | Pagliuca et al. |
| 7,067,583 B2 | 6/2006 | Chen |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,093,599 B2 | 8/2006 | Chen |
| 7,100,614 B2 | 9/2006 | Stevens et al. |
| 7,101,353 B2 | 9/2006 | Lui et al. |
| 7,105,009 B2 | 9/2006 | Johnson et al. |
| 7,105,607 B2 | 9/2006 | Chen |
| 7,112,185 B2 | 9/2006 | Hart et al. |
| 7,118,528 B1 | 10/2006 | Piskun |
| 7,134,929 B2 | 11/2006 | Chen |
| 7,153,261 B2 | 12/2006 | Wenchell |
| 7,163,510 B2 | 1/2007 | Kahle et al. |
| 7,192,436 B2 | 3/2007 | Sing et al. |
| 7,193,002 B2 | 3/2007 | Chen |

(56) References Cited

U.S. PATENT DOCUMENTS

| | | |
|---|---|---|
| 7,195,590 B2 | 3/2007 | Butler et al. |
| 7,214,185 B1 | 5/2007 | Rosney et al. |
| 7,217,277 B2 | 5/2007 | Parihar et al. |
| 7,222,380 B2 | 5/2007 | Chen |
| 7,223,257 B2 | 5/2007 | Shubayev et al. |
| 7,223,278 B2 | 5/2007 | Davison et al. |
| 7,226,484 B2 | 6/2007 | Chen |
| 7,235,062 B2 | 6/2007 | Brustad |
| 7,235,084 B2 | 6/2007 | Skakoon et al. |
| 7,238,154 B2 | 7/2007 | Ewers et al. |
| 7,244,244 B2 | 7/2007 | Racenet et al. |
| 7,276,075 B1 | 10/2007 | Callas et al. |
| 7,290,367 B2 | 11/2007 | Chen |
| 7,294,103 B2 | 11/2007 | Bertolero et al. |
| 7,297,106 B2 | 11/2007 | Yamada et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,338,473 B2 | 3/2008 | Campbell et al. |
| 7,344,546 B2 | 3/2008 | Wulfman et al. |
| 7,344,547 B2 | 3/2008 | Piskun |
| 7,344,568 B2 | 3/2008 | Chen |
| 7,377,898 B2 | 5/2008 | Ewers et al. |
| 7,390,317 B2 | 6/2008 | Taylor et al. |
| 7,393,322 B2 | 7/2008 | Wenchell |
| 7,412,977 B2 | 8/2008 | Fields et al. |
| 7,445,597 B2 | 11/2008 | Butler et al. |
| 7,473,221 B2 | 1/2009 | Ewers et al. |
| 7,481,765 B2 | 1/2009 | Ewers et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,578,832 B2 | 8/2009 | Johnson |
| 7,645,232 B2 | 1/2010 | Shluzas |
| 7,650,887 B2 | 1/2010 | Nguyen et al. |
| 7,661,164 B2 | 2/2010 | Chen |
| 7,704,207 B2 | 4/2010 | Albrecht et al. |
| 7,717,847 B2 | 5/2010 | Smith |
| 7,727,146 B2 | 6/2010 | Albrecht et al. |
| 7,727,255 B2 | 6/2010 | Taylor et al. |
| 7,736,306 B2 | 6/2010 | Brustad et al. |
| 7,749,415 B2 | 7/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,841,765 B2 | 11/2010 | Keller |
| 7,850,667 B2 | 12/2010 | Gresham |
| 7,867,164 B2 | 1/2011 | Butler et al. |
| 7,878,974 B2 | 2/2011 | Brustad et al. |
| 7,896,889 B2 | 3/2011 | Mazzocchi et al. |
| 7,909,760 B2 | 3/2011 | Albrecht et al. |
| 7,930,782 B2 | 4/2011 | Chen |
| 7,998,068 B2 | 8/2011 | Bonadio et al. |
| 8,021,296 B2 | 9/2011 | Bonadio |
| 8,317,690 B2 | 11/2012 | Ransden |
| 8,343,047 B2 * | 1/2013 | Albrecht ............... A61B 1/32 600/206 |
| RE44,380 E | 7/2013 | de la Torre et al. |
| 8,574,153 B2 | 11/2013 | Richard |
| RE44,790 E | 3/2014 | de la Torre et al. |
| 2001/0037053 A1 | 11/2001 | Bonadio et al. |
| 2001/0047188 A1 | 11/2001 | Bonadio et al. |
| 2002/0002324 A1 | 1/2002 | McManus |
| 2002/0010389 A1 | 1/2002 | Butler et al. |
| 2002/0013542 A1 | 1/2002 | Bonadio et al. |
| 2002/0016607 A1 | 2/2002 | Bonadio et al. |
| 2002/0026230 A1 | 2/2002 | Moll et al. |
| 2002/0038077 A1 | 3/2002 | de la Torre et al. |
| 2002/0049276 A1 | 4/2002 | Zwick |
| 2002/0072762 A1 | 6/2002 | Bonadio et al. |
| 2002/0111536 A1 | 8/2002 | Cuschieri et al. |
| 2003/0004253 A1 | 1/2003 | Chen |
| 2003/0014076 A1 | 1/2003 | Mollenauer et al. |
| 2003/0028179 A1 | 2/2003 | Piskun |
| 2003/0040711 A1 | 2/2003 | Racenet et al. |
| 2003/0078478 A1 | 4/2003 | Bonadio et al. |
| 2003/0139756 A1 | 7/2003 | Brustad |
| 2003/0167040 A1 | 9/2003 | Bacher et al. |
| 2003/0187376 A1 | 10/2003 | Rambo |
| 2003/0192553 A1 | 10/2003 | Rambo |
| 2003/0225392 A1 | 12/2003 | McMichael et al. |
| 2003/0236505 A1 | 12/2003 | Bonadio et al. |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049099 A1 | 3/2004 | Ewers et al. |
| 2004/0049100 A1 | 3/2004 | Butler |
| 2004/0054353 A1 | 3/2004 | Taylor |
| 2004/0063833 A1 | 4/2004 | Chen |
| 2004/0068232 A1 | 4/2004 | Hart et al. |
| 2004/0070187 A1 | 4/2004 | Chen |
| 2004/0072942 A1 | 4/2004 | Chen |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor et al. |
| 2004/0111061 A1 | 6/2004 | Curran |
| 2004/0127772 A1 | 7/2004 | Ewers et al. |
| 2004/0138529 A1 | 7/2004 | Wiltshire et al. |
| 2004/0143158 A1 | 7/2004 | Hart et al. |
| 2004/0154624 A1 | 8/2004 | Bonadio et al. |
| 2004/0167559 A1 | 8/2004 | Taylor et al. |
| 2004/0173218 A1 | 9/2004 | Yamada et al. |
| 2004/0215063 A1 | 10/2004 | Bonadio et al. |
| 2004/0230161 A1 | 11/2004 | Zeiner |
| 2004/0243144 A1 | 12/2004 | Bonadio et al. |
| 2004/0249248 A1 | 12/2004 | Bonadio et al. |
| 2004/0254426 A1 | 12/2004 | Wenchell |
| 2004/0260244 A1 | 12/2004 | Piechowicz et al. |
| 2004/0267096 A1 | 12/2004 | Caldwell et al. |
| 2005/0020884 A1 | 1/2005 | Hart et al. |
| 2005/0033246 A1 * | 2/2005 | Ahlberg ............ A61B 17/3423 604/264 |
| 2005/0059865 A1 | 3/2005 | Kahle et al. |
| 2005/0065475 A1 | 3/2005 | Hart et al. |
| 2005/0065543 A1 | 3/2005 | Kahle et al. |
| 2005/0080319 A1 | 4/2005 | Dinkler, II et al. |
| 2005/0090713 A1 | 4/2005 | Gonzales et al. |
| 2005/0090716 A1 | 4/2005 | Bonadio et al. |
| 2005/0090717 A1 | 4/2005 | Bonadio et al. |
| 2005/0096695 A1 | 5/2005 | Olich |
| 2005/0131349 A1 | 6/2005 | Albrecht et al. |
| 2005/0137615 A1 * | 6/2005 | Mapes ............ A61B 17/32072 606/159 |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson et al. |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0222582 A1 | 10/2005 | Wenchell |
| 2005/0240082 A1 | 10/2005 | Bonadio et al. |
| 2005/0241647 A1 | 11/2005 | Nguyen |
| 2005/0251124 A1 | 11/2005 | Zvuloni et al. |
| 2005/0261720 A1 | 11/2005 | Caldwell et al. |
| 2005/0267419 A1 | 12/2005 | Smith |
| 2005/0277946 A1 | 12/2005 | Greenhalgh |
| 2005/0283050 A1 | 12/2005 | Gundlapalli et al. |
| 2005/0288558 A1 | 12/2005 | Ewers et al. |
| 2005/0288634 A1 | 12/2005 | O'Heeron et al. |
| 2006/0020164 A1 | 1/2006 | Butler et al. |
| 2006/0020241 A1 | 1/2006 | Piskun et al. |
| 2006/0030755 A1 | 2/2006 | Ewers et al. |
| 2006/0041270 A1 | 2/2006 | Lenker |
| 2006/0047284 A1 | 3/2006 | Gresham |
| 2006/0047293 A1 | 3/2006 | Haberland et al. |
| 2006/0052669 A1 | 3/2006 | Hart |

(56) References Cited

U.S. PATENT DOCUMENTS

| | | |
|---|---|---|
| 2006/0084842 A1 | 4/2006 | Hart et al. |
| 2006/0106402 A1 | 5/2006 | McLucas |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0241651 A1 | 10/2006 | Wilk |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh, II et al. |
| 2006/0258899 A1 | 11/2006 | Gill et al. |
| 2006/0264706 A1 | 11/2006 | Piskun |
| 2006/0270911 A1 | 11/2006 | Voegele et al. |
| 2007/0004968 A1 | 1/2007 | Bonadio et al. |
| 2007/0049966 A1 | 3/2007 | Bonadio et al. |
| 2007/0088202 A1 | 4/2007 | Albrecht et al. |
| 2007/0088204 A1 | 4/2007 | Albrecht |
| 2007/0093695 A1 | 4/2007 | Bonadio et al. |
| 2007/0118175 A1 | 5/2007 | Butler et al. |
| 2007/0149859 A1 | 6/2007 | Albrecht |
| 2007/0151566 A1 | 7/2007 | Kahle et al. |
| 2007/0156023 A1 | 7/2007 | Frasier et al. |
| 2007/0185387 A1 | 8/2007 | Albrecht et al. |
| 2007/0203398 A1 | 8/2007 | Bonadio et al. |
| 2007/0208312 A1 | 9/2007 | Norton et al. |
| 2007/0255219 A1 | 11/2007 | Vaugh et al. |
| 2007/0270752 A1 | 11/2007 | Labombard |
| 2007/0299387 A1 | 12/2007 | Williams et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097163 A1 | 4/2008 | Butler et al. |
| 2008/0200767 A1 | 8/2008 | Ewers et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0012477 A1 | 1/2009 | Norton et al. |
| 2009/0036745 A1 | 2/2009 | Bonadio et al. |
| 2009/0069837 A1 | 3/2009 | Bonadio et al. |
| 2009/0093683 A1 | 4/2009 | Richard et al. |
| 2009/0093752 A1 | 4/2009 | Richard et al. |
| 2009/0131754 A1 | 5/2009 | Ewers et al. |
| 2009/0137879 A1 | 5/2009 | Ewers et al. |
| 2009/0149714 A1 | 6/2009 | Bonadio |
| 2009/0182279 A1 | 7/2009 | Wenchell et al. |
| 2009/0182282 A1 | 7/2009 | Okihisa |
| 2009/0187079 A1 | 7/2009 | Albrecht et al. |
| 2009/0227843 A1 | 9/2009 | Smith et al. |
| 2009/0292176 A1 | 11/2009 | Bonadio et al. |
| 2009/0326330 A1 | 12/2009 | Bonadio et al. |
| 2010/0063362 A1 | 3/2010 | Bonadio et al. |
| 2010/0063364 A1 | 3/2010 | Bonadio et al. |
| 2010/0081880 A1 | 4/2010 | Widenhouse et al. |
| 2010/0081881 A1 | 4/2010 | Murray et al. |
| 2010/0081995 A1 | 4/2010 | Widenhouse et al. |
| 2010/0100043 A1 | 4/2010 | Racenet |
| 2010/0113882 A1 | 5/2010 | Widenhouse et al. |
| 2010/0217087 A1 | 8/2010 | Bonadio et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0249525 A1 | 9/2010 | Shelton, IV et al. |
| 2010/0249694 A1 | 9/2010 | Choi et al. |
| 2010/0261972 A1 | 10/2010 | Widenhouse et al. |
| 2010/0261975 A1 | 10/2010 | Huey et al. |
| 2010/0286484 A1 | 11/2010 | Stellon et al. |
| 2010/0298646 A1 | 11/2010 | Stellon et al. |
| 2011/0021877 A1 | 1/2011 | Fortier et al. |
| 2011/0028891 A1 | 2/2011 | Okoniewski |
| 2011/0034935 A1 | 2/2011 | Kleyman |
| 2011/0034946 A1 | 2/2011 | Kleyman |
| 2011/0034947 A1 | 2/2011 | Kleyman |
| 2011/0071462 A1 | 3/2011 | Ewers et al. |
| 2011/0071463 A1 | 3/2011 | Ewers et al. |
| 2012/0095297 A1 | 4/2012 | Dang et al. |

FOREIGN PATENT DOCUMENTS

| | | |
|---|---|---|
| DE | 37 39 532 | 12/1988 |
| DE | 37 37 121 | 5/1989 |
| DE | 296 00 939 | 6/1996 |
| DE | 19828099 | 12/1999 |
| EP | 0 113 520 | 7/1984 |
| EP | 0 142 262 | 5/1985 |
| EP | 0 517 248 | 12/1992 |
| EP | 0 537 768 | 4/1993 |
| EP | 0 807 416 | 11/1997 |
| EP | 0 849 517 | 6/1998 |
| EP | 0950376 | 10/1999 |
| EP | 1 118 657 | 7/2001 |
| EP | 1 125 552 | 8/2001 |
| EP | 1 312 318 | 5/2003 |
| EP | 1 407 715 | 4/2004 |
| EP | 2 044 889 | 4/2009 |
| EP | 1 948 047 B1 | 9/2010 |
| EP | 2 272 449 A2 | 1/2011 |
| EP | 2 272 450 A2 | 1/2011 |
| EP | 2 340 792 | 7/2011 |
| FR | 1456623 | 9/1966 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1482857 | 8/1977 |
| GB | 1496696 | 12/1977 |
| GB | 2071502 | 9/1981 |
| GB | 2255019 | 10/1992 |
| GB | 2275420 | 8/1994 |
| GB | 2298906 | 9/1996 |
| IE | 930649 | 9/1993 |
| IE | 930650 | 9/1993 |
| IE | S940150 | 2/1994 |
| IE | S940613 | 8/1994 |
| IE | S940960 | 12/1994 |
| IE | S950055 | 1/1995 |
| IE | S950266 | 4/1995 |
| IE | S75368 | 8/1997 |
| IE | S960196 | 8/1997 |
| IE | S970810 | 11/1997 |
| IE | 991010 | 7/2000 |
| IE | 990218 | 11/2000 |
| IE | 990219 | 11/2000 |
| IE | 990220 | 11/2000 |
| IE | 990660 | 2/2001 |
| IE | 990795 | 3/2001 |
| JP | 10-108868 | 4/1998 |
| JP | 11-290327 | 10/1999 |
| JP | 2001-61850 | 3/2001 |
| JP | 2002-28163 | 1/2002 |
| JP | 02003 235879 A | 8/2003 |
| JP | 2004-195037 | 7/2004 |
| SU | 1342485 | 1/1997 |
| WO | WO 86/06272 | 11/1986 |
| WO | WO 86/06316 | 11/1986 |
| WO | WO 92/11880 | 7/1992 |
| WO | WO 92/21292 | 12/1992 |
| WO | WO 93/05740 | 4/1993 |
| WO | WO 93/14801 | 8/1993 |
| WO | WO 94/04067 | 3/1994 |
| WO | WO 94/22357 | 10/1994 |
| WO | WO 95/05207 | 2/1995 |
| WO | WO 95/07056 | 3/1995 |
| WO | WO 95/22289 | 8/1995 |
| WO | WO 95/24864 | 9/1995 |

(56) References Cited

FOREIGN PATENT DOCUMENTS

| | | |
|---|---|---|
| WO | WO 95/27445 | 10/1995 |
| WO | WO 95/27468 | 10/1995 |
| WO | WO 96/36283 | 11/1996 |
| WO | WO 97/11642 | 4/1997 |
| WO | WO 97/32514 | 9/1997 |
| WO | WO 97/32515 | 9/1997 |
| WO | WO 97/42889 | 11/1997 |
| WO | WO 98/19853 | 5/1998 |
| WO | WO 98/35614 | 8/1998 |
| WO | WO 98/48724 | 11/1998 |
| WO | WO 99/03416 | 1/1999 |
| WO | WO 99/15068 | 4/1999 |
| WO | WO 99/16368 | 4/1999 |
| WO | WO 99/22804 | 5/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/26559 | 4/2001 |
| WO | WO 01/45568 | 6/2001 |
| WO | WO 01/49363 | 7/2001 |
| WO | WO 01/91652 | 12/2001 |
| WO | WO 02/07611 | 1/2002 |
| WO | WO 02/17800 | 3/2002 |
| WO | WO 02/34108 | 5/2002 |
| WO | WO 03/011153 | 2/2003 |
| WO | WO 03/011551 | 2/2003 |
| WO | WO 03/026512 | 4/2003 |
| WO | WO 03/032819 | 4/2003 |
| WO | WO 03/034908 | 5/2003 |
| WO | WO 03/061480 | 7/2003 |
| WO | WO 03/077726 | 9/2003 |
| WO | WO 03/103548 | 12/2003 |
| WO | WO 2004/026153 | 4/2004 |
| WO | WO 2004/030547 | 4/2004 |
| WO | WO 2004/075730 | 9/2004 |
| WO | WO 2004/075741 | 9/2004 |
| WO | WO 2004/075930 | 9/2004 |
| WO | WO 2005/009257 | 2/2005 |
| WO | WO 2005/013803 A2 | 2/2005 |
| WO | WO 2005/034766 | 4/2005 |
| WO | WO 2005/089661 | 9/2005 |
| WO | WO 2006/040748 | 4/2006 |
| WO | WO 2006/059318 | 6/2006 |
| WO | WO 2006/100658 | 9/2006 |
| WO | WO 2007/044849 | 4/2007 |
| WO | WO 2008/015566 | 2/2008 |
| WO | WO 2008/093313 | 8/2008 |
| WO | WO 2008/121294 | 10/2008 |
| WO | WO 2010/045253 | 4/2010 |
| WO | WO 2010/082722 | 7/2010 |
| WO | WO 2010/104259 | 9/2010 |

OTHER PUBLICATIONS

U.S. Appl. No. 10/436,522, filed May 13, 2003; Title: Laparoscopic Illumination Apparatus and Method, now USPN 6,939,296 issued Sep. 6, 2005.

U.S. Appl. No. 10/399,209, filed Aug. 22, 2003; Title: Wound Retraction Apparatus and Method, now USPN 6,958,037 issued Oct. 25, 2005.

U.S. Appl. No. 11/218,412, filed Sep. 1, 2005; Title: Wound Retraction Apparatus and Method, now USPN 7,238,154 issued Jul. 3, 2007.

U.S. Appl. No. 10/399,057, filed Apr. 11, 2003; Title: Sealed Surgical Access Device, now USPN 7,052,454 issued May 30, 2006.

U.S. Appl. No. 10/666,579, filed Sep. 17, 2003; Title: Surgical Instrument Access Device, now USPN 7,163,510 issued Jan. 16, 2007.

U.S. Appl. No. 10/052,297, filed Jan. 18, 2002; Title: Hand Access Port Device, now USPN 6,908,430 issued Jun. 21, 2005.

U.S. Appl. No. 08/015,765, filed Feb. 10, 1993; Title: Gas-Tight Seal Accomodating Surgical Instruments With a Wide Range of Diameters, now USPN 5,407,433 issued Apr. 18, 1995.

U.S. Appl. No. 08/040,373, filed Mar. 30, 1993; Title: Gas-Tight Seal Accomodating Surgical Instruments With a Wide Range of Diameters, now USPN 5,411,483 issued May 2, 1995.

U.S. Appl. No. 10/902,756, filed Jul. 29, 2004; Title: Hand Access Port Device, now abandoned.

U.S. Appl. No. 10/802,125, filed Mar. 15, 2004; Title: Surgical Guide Valve, now abandoned.

U.S. Appl. No. 10/516,198, filed Nov. 30, 2004; Title: Wound Retractor, now USPN 7,650,887 issued Jan. 26, 2010.

U.S. Appl. No. 10/927,551, filed Aug. 25, 2004; Title: Surgical Access System, now abandoned.

U.S. Appl. No. 11/244,647, filed Oct. 5, 2005; Title: Surgical Access Apparatus and Method, now USPN 7,481,765 issued Jan. 27, 2009.

U.S. Appl. No. 11/548,746, filed Oct. 12, 2006; Title: Method of Making a Hand Access Laparoscopic Device, now USPN 7,749,415 issued Jul. 6, 2010.

U.S. Appl. No. 11/548,765, filed Oct. 12, 2006; Title: Split Hoop Wound Retractor, now USPN 7,815,567 issued Oct. 26, 2010.

U.S. Appl. No. 11/548,767, filed Oct. 12, 2006; Title: Circular Surgical Retractor now USPN 7,704,207 issued Apr. 27, 2010.

U.S. Appl. No. 11/548,781, filed Oct. 12, 2006; Title: Wound Retractor With Gel Cap, now USPN 7,727,146 issued Jun. 1, 2010.

U.S. Appl. No. 11/548,955, filed Oct. 12, 2006; Title: Hand Access Laparoscopic Device, now USPN 7,736,306 issued Jun. 15, 2010.

U.S. Appl. No. 11/755,305, filed May 30, 2007; Title: Wound Retraction Apparatus and Method, now USPN 7,377,898 issued May 27, 2008.

U.S. Appl. No. 11/548,758, filed Oct. 12, 2007; Title: Split Hoop Wound Retractor With Gel Pad, now USPN 7,909,760 issued Mar. 22, 2011.

U.S. Appl. No. 12/693,242, filed Jan. 1, 2010; Title: Wound Retractor, now USPN 7,913,697 issued Mar. 29, 2011.

U.S. Appl. No. 12/768,328, filed Apr. 27, 2010; Title: Circular Surgical Retractor, now USPN 7,892,172 issued Feb. 22, 2011.

U.S. Appl. No. 12/791,666, filed Jun. 1, 2010; Title: Wound Retractor With Gel Cap, now USPN 7,883,461 issued Feb. 8, 2011.

U.S. Appl. No. 12/815,986, filed Jun. 15, 2010; Title: Hand Access Laparoscopic Device, now USPN 7,878,974 issued Feb. 1, 2011.

U.S. Appl. No. 10/695,295, filed Oct. 28, 2003; Title: Surgical Gel Seal.

U.S. Appl. No. 11/132,741, filed May 18, 2005; Title: Gas-Tight Seal Accomodating Surgical Instruments With a Wide Range of Diameters.

U.S. Appl. No. 11/245,709, filed Oct. 7, 2005; Title: Surgical Access System.

U.S. Appl. No. 11/330,661, filed Jan. 12, 2006; Title: Sealed Surgical Access Device.

U.S. Appl. No. 11/564,409, filed Nov. 29, 2006; Title: Surgical Instrument Access Device.

U.S. Appl. No. 12/108,400, filed Apr. 23, 2008; Title: Wound Retraction Apparatus and Method.

U.S. Appl. No. 12/119,371, filed May 12, 2008; Title: Surgical Retractor With Gel Pad.

U.S. Appl. No. 12/119,414, filed May 12, 2008; Title: Surgical Retractor.

U.S. Appl. No. 12/358,080, filed Jan. 22, 2009; Title: Surgical Instrument Access Device.

U.S. Appl. No. 12/360,634, filed Jan. 27, 2009; Title: Surgical Access Apparatus and Method.

U.S. Appl. No. 12/360,710, filed Jan. 27, 2009; Title: Surgical Access Apparatus and Method.

(56) References Cited

OTHER PUBLICATIONS

U.S. Appl. No. 12/578,422, filed Oct. 13, 2009; Title: Single Port Access System.
U.S. Appl. No. 12/905,932, filed Oct. 15, 2010; Title: Split Hoop Wound Retractor.
U.S. Appl. No. 12/960,449, filed Dec. 3, 2010; Title: Surgical Access Apparatus and Method.
U.S. Appl. No. 12/960,458, filed Dec. 3, 2010; Title: Surgical Access Apparatus and Method.
U.S. Appl. No. 13/006,727, filed Jan. 14, 2011; Title: Hand Access Laparoscopic Device.
U.S.Appl. No. 13/008,728, filed Jan. 18, 2011; Title: Wound Retractor With Gel Cap.
U.S. Appl. No. 13/023,334, filed Feb. 8, 2011; Title: Circular Surgical Retractor.
U.S. Appl. No. 13/031,892, filed Feb. 22, 2011; Title: Wound Retractor.
U.S. Appl. No. 13/050,042, filed Mar. 17, 2011; Title: Split Hoop Wound Retractor With Gel Pad.
U.S. Appl. No. 10/446,365, filed May 28, 2003; Title: Screw-Type Seal With Inflatable Membrane.
U.S. Appl. No. 12/004,439, filed Dec. 20, 2007; Title: Skin Seal.
U.S. Appl. No. 12/004,441, filed Dec. 20, 2007; Title: Screw-Type Skin Seal With Inflatable Membrane.
U.S. Appl. No. 12/607,667, filed Oct. 28, 2009; Title: Screw-Type Skin Seal With Inflatable Membrane.
U.S. Appl. No. 10/965,217, filed Oct. 15, 2004; Title: Surgical Sealing Device.
U.S. Appl. No. 10/981,730, filed Nov. 5, 2004; Title: Surgical Sealing Device.
U.S. Appl. No. 11/246,909, filed Oct. 11, 2005; Title: Instrument Access Device.
U.S. Appl. No. 11/291,089, filed Dec. 1, 2005; Title: A Surgical Sealing Device.
U.S. Appl. No. 11/486,383, filed Jul. 14, 2006; Title: Wound Retractor.
U.S. Appl. No. 11/785,752, filed Apr. 19, 2007; Title: Instrument Access Device.
U.S. Appl. No. 12/244,024, filed Oct. 2, 2008; Title: Seal Anchor for Use in Surgical Procedures.
U.S. Appl. No. 12/578,832, filed Oct. 14, 2009; Title: Flexible Access Device for Use in Surgical Procedure.
U.S. Appl. No. 12/706,043, filed Feb. 16, 2010; Title: Flexible Port Seal.
U.S. Appl. No. 12/719,341, filed Mar. 8, 2010; Title: Foam Port and Introducer Assembly.
U.S. Appl. No. 10/895,546, filed Jul. 21, 2004; Title: Laparoscopic.
U.S. Appl. No. 10/913,565, filed Aug. 5, 2004; Title: Surgical Device With Tack-Free Gel and Method of Manufacture.
Dexterity Protractor Instruction Manual by Dexterity Surgical, Inc., dated 1999.
European Patent Office, European Search Report for European Application No. EP 10 18 4681, entitled "Wound Retraction Apparatus and Method",dated Nov. 22, 2010.
European Patent Office, European Search Report for European Application No. EP 10 18 4608, entitled "Wound Retraction Apparatus and Method", dated Nov. 22, 2010.
European Patent Office, European Search Report for European Application No. EP 10 18 4648, entitled "Wound Retraction Apparatus and Method", dated Nov. 22, 2010.
European Patent Office, European Search Report for European Application No. EP 10 18 4731, entitled "Wound Retraction Apparatus and Method", dated Nov. 22, 2010.
European Patent Office, European Search Report for European Application No. EP 10 18 4661, entitled "Wound Retraction Apparatus and Method", dated Nov. 22, 2010.
European Patent Office, European Search Report for European Application No. EP 10 18 4677, entitled "Wound Retraction Apparatus and Method", dated Nov. 22, 2010.
European Patent Office, European Search Report for European Application No. EP 10 18 9325, entitled "Split Hoop Wound Retractor", dated Dec. 14, 2010.
European Patent Office, European Search Report for European Application No. EP 10 18 9327, entitled "Split Hoop Wound Retractor", dated Dec. 14, 2010.
European Patent Office, European Search Report for European Application No. EP 10 18 9328, entitled "Split Hoop Wound Retractor", dated Dec. 15, 2010.
European Patent Office, European Search Report for European Application No. EP 04 00 2888, entitled "Hand Access Port Device", dated Sep. 10, 2004.
European Patent Office, European Search Report for European Application No. EP 04 00 2889, entitled "Hand Access Port Device", dated Sep. 13, 2004.
European Patent Office, International Search Report and the Written Opinion of the International Searching Authority for International Application No. PCT/US2006/040154, mailed Jan. 30, 2007.
European Patent Office, International Search Report and the Written Opinion of the International Searching Authority for International Application No. PCT/US2006/040073, mailed Jan. 26, 2007.
European Patent Office, International Search Report and the Written Opinion of the International Searching Authority for International Application No. PCT/US2006/039905, mailed Jan. 17, 2007.
European Patent Office, International Search Report and the Written Opinion of the International Searching Authority for International Application No. PCT/US2006/039883, mailed Jan. 31, 2007.
European Patent Office, International Search Report and the Written Opinion of the International Searching Authority for International Application No. PCT/US2006/039800, mailed Apr. 16, 2007.
European Patent Office, International Search Report and the Written Opinion of the International Searching Authority for International Application No. PCT/US2006/039799, mailed Mar. 27, 2007.
European Patent Office, European Search Report for European Application No. EP 08253236 dated Feb. 10, 2009.
Horigame, et al., Silicone Rumen Cannula with a Soft Cylindrical Part and a Hard Flange, Journal of Dairy Science, Nov. 1989, vol. 72, No. 11, pp. 3230-3232.
Horigame, et al., Technical Note: Development of Duodoenal Cannula for Sheep, Journal of Animal Science, Apr. 1992, vol. 70, Issue 4, pp. 1216-1219.
International Searching Authority/US, International Search Report and the Written Opinion of the International Searching Authority for International Application No. PCT/US04/05484, mailed on Nov. 12, 2004.
International Searching Authority/US, International Search Report and the Written Opinion of the International Searching Authority for International Application No. PCT/US01/29682, mailed on Jun. 14, 2002.
Mcsweeney, Cannulation of the Rumen in Cattle and Buffaloes, Australian Veterniary Journal, Aug. 1989, vol. 66, No. 8, pp. 266-268.
Neil Sheehan, Supplemental Expert Report of Neil Sheehan, Re: U.S. Pat. No. 5,741,298, United States District Court for the Central District of California, Civil Action No. SACV 03-1322 JVS, Aug. 9, 2005.
Office Action in co-pending U.S. Appl. No. 12/360,634, dated Jan. 24, 2011 in 12 pages.
Office Action in co-pending U.S. Appl. No. 12/360,710, dated Jan. 24, 2011 in 12 pages.
Technical Note: Development of Duodenal Cannula for Sheep, Faculty of Agriculture and School of Medicine Tohokju University, Sendai 981, Japan, dated 1992.
The International Bureau of WIPO, International Preliminary Report on Patentability for International Application No. PCT/US2004/028250, dated Aug. 29, 2006.
The International Bureau of WIPO, International Preliminary Report on Patentability for International Application No. PCT/US2006/039799, dated Apr. 16, 2008.
The International Bureau of WIPO, International Preliminary Report on Patentability for International Application No. PCT/US2006/039800 dated Apr. 16, 2008.

(56) References Cited

OTHER PUBLICATIONS

Yamazaki, et al., Diurnal Changes in the Composition of Abomasal Digesta in Fasted and Fed Sheep, The Tohoki Journal of Agricultural Research, Mar. 1987, vol. 37, No. 3-4, pp. 49-58.

Kagaya, Laparascopic cholecystecomy via two ports, using the "Twin-Port" system, J. Hepatobiliary Pancreat Surg (2001) 8:76-80, dated Feb. 20, 2001.

Declaration of John R. Brustad dated Dec. 10, 2009, submitted in U.S. Appl. No. 11/548,955, including Appendices A-D regarding product sales brochures and production drawings from 2001 and 2005.

International Search Report and Written Opinion for PCT/IE2005/000113, mailed on Feb. 22, 2006.

International Searching Authority-US, International Search Report and Written Opinion of the International Searching Authority for International Application No. PCT/US04/25511, mailed Nov. 7, 2007.

International Bureau of WIPO, International Report on Patentability for International Application No. PCT/US04/25511, mailed Dec. 6, 2007.

International Search Report and Written Opinion for PCT/IE2007/000050 mailed on Aug. 13, 2007.

The International Searching Authority, The International Search Report and Written Opinion of the International Searching Authority for International Application No. PCT/US08/63445, mailed Sep. 29, 2008.

The International Searching Authority, The International Search Report and Written Opinion of the International Searching Authority for International Application No. PCT/US08/063463 mailed Sep. 10, 2008.

The International Bureau of WIPO, International Preliminary Report on Patentability for International Application No. PCT/US2008/063463, entitled "Surgical Retractor", dated Nov. 17, 2009.

The International Bureau of WIPO, International Preliminary Report on Patentability for International Application No. PCT/US08/63445, entitled "Surgical Retractor with Gel Pad", dated Nov. 17, 2009.

International Searching Authority—European Patent Office, The International Search Report and Written Opinion for International Application No. PCT/US2011/054266, mailed Feb. 9, 2012.

European Patent Office, European Search Report for European U.S. Pat. No. 11172709.5, dated Aug. 16, 2011.

European Patent Office, European Search Report for European U.S. Pat. No. 11172706.1, dated Aug. 16, 2011.

European Patent Office, European Search Report for European U.S. Pat. No. 12151288, dated Feb. 10, 2012.

European Patent Office, European Search Report for European U.S. Pat. No. 08755332, dated Apr. 18, 2012.

European Patent Office, Supplementary European Search Report for European Patent Application No. 08755322, dated Apr. 18, 2012.

European Patent Office, Supplementary European Search Report for European Patent Application No. 08755336, dated Jun. 15, 2012.

Harold W. Harrower, M.D., Isolation of Incisions into Body Cavities, The American Journal of Surgery, vol. 116, pp. 824-826, Dec. 1968.

International Searching Authority—European Patent Office, The International Search Report and Written Opinion for International Application No. PCT/US2013/037213, mailed Jul. 3, 2013.

The International Bureau of WIPO, International Preliminary Report on Patentability for International Application No. PCT/US2011/054266, titled, Natural Orifice Surgery System dated Apr. 2, 2013.

International Searching Authority—European Patent Office, The International Search Report and Written Opinion for International Application No. PCT/US2015/040798, mailed Dec. 14, 2015, 21 pgs.

* cited by examiner

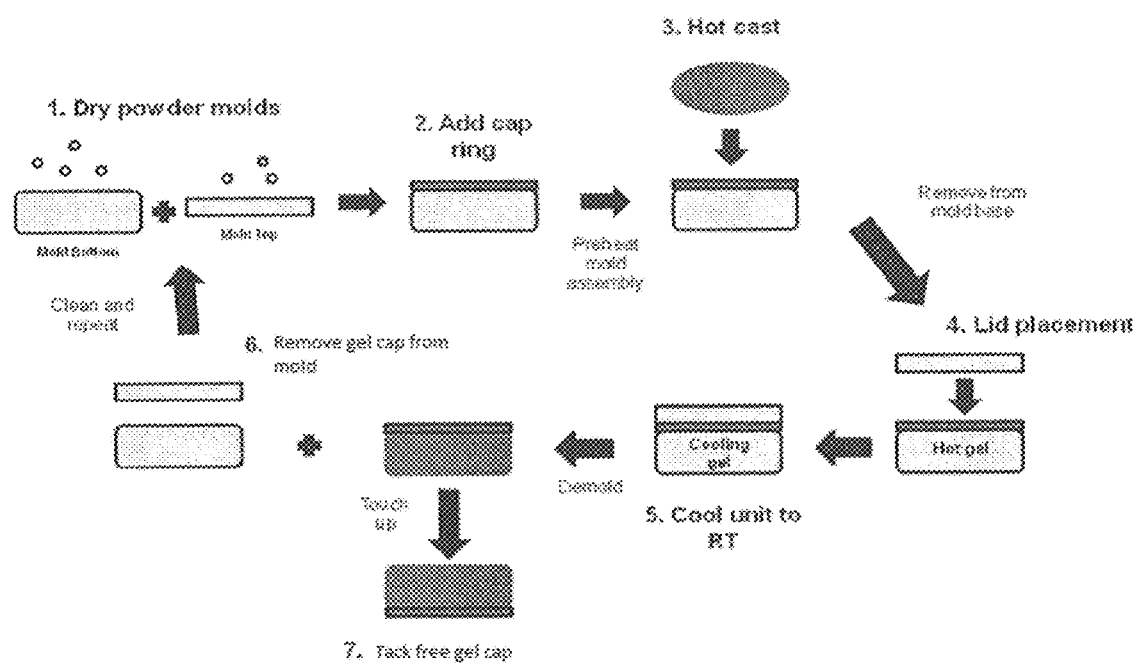
Figure 16 – Flow diagram of method for manufacturing a tack-free gel cap

GELS HAVING PERMANENT TACK FREE COATINGS AND METHOD OF MANUFACTURE

CROSS REFERENCE TO RELATED APPLICATIONS

This application claims the benefit of U.S. Application No. 62/026,317, filed Jul. 18, 2014, the entire disclosure of which is incorporated by reference.

BACKGROUND

Technical Field

This invention generally relates to gels having tack-free coatings and, more specifically, to methods for manufacturing gels having a permanent tack-free coating. Such gels are particularly useful when incorporated into surgical devices such as access ports.

Description of the Related Art

A "gel" is often defined as a semisolid condition of a precipitated or coagulated colloid. Despite its derivation from the Latin word gelare "to freeze," gels differ widely in their fluid/solid characteristics, ranging from more fluid gels, such as those found in gel toothpastes, to more solid gels, such as those used in bicycle seat pads.

Gels tending toward the "solid" end of the spectrum are commonly used to facilitate load distribution. Gels enhance this function by offering a high degree of compliance, which basically increases the amount of area available to support a load. With an increased area of support, the load is accommodated at a considerably reduced pressure. Particularly where the human body is involved, a reduced pressure is desirable in order to maintain capillary blood flow in body tissue. It is with this in mind that gels are commonly used for bicycle seats, wrist pads, insole supports, as well as elbow and shoulder pads.

Gels have been of particular interest in the formation of seals, where the high compliance and extensive elongation of the gel are of considerable value. Such is the case with seals used in trocars and other surgical access devices, including access ports, in which a seal must be formed both in the presence of a surgical instrument (or surgeon's hand) and in the absence of a surgical instrument.

In general, an access device is a surgical device intended to provide access for surgical instruments across a body wall, such as the abdominal wall, and into a body cavity, such as the abdominal cavity. Often, the body cavity is pressurized with a gas, typically carbon dioxide, to enlarge the operative volume of the working environment. Under these conditions, the access device must include appropriate seals to inhibit loss of the pressurizing gas, both with and without a surgical instrument disposed through the seal. Seals formed from a gel material provide a high degree of compliance, significant tear strength and exceptional elongation and thus are particularly useful in access ports.

While the advantageous properties of gels have made them candidates for many applications, one disadvantage has seriously limited their use. Most gels are extremely tacky. This characteristic alone makes them difficult to manufacture and aggravating to use.

Attempts have been made to produce gels that are naturally non-tacky. Such naturally non-tacky gels, however, are not particularly heat tolerant, as low amounts of heat can rapidly cause the materials to take a set and distort, particularly under compressive loads. This can occur over an extended period of time, for example, even at normal room temperatures.

Attempts have been made to enclose tacky gels in a non-tacky pouch. This has also tended to mask the advantageous properties and to significantly increase manufacturing costs.

Lubricants such as silicone oil have been applied to the surface to reduce tackiness. Unfortunately, these lubricants tend to dry out over time leaving the gel in its natural tacky state.

Powders, including starch, have been applied to the tacky surfaces with results limited in both duration and effect. In addition, the use of a starch based powder as a blocking agent and the application of the blocking agent during production increases the cost of manufacture and may necessitate additional cleaning steps, greatly increasing the manufacturing time for producing powdered gel products.

Starch blocking agents further complicate manufacturing by providing a growth medium for bacteria and other microorganisms. Medical devices incorporating gels are typically irradiated at a higher than normal sterilization dose to compensate for this. However, higher sterilization doses are known to compromise mechanical properties of the device materials. Also, because corn starch is not permanently fused to the gel surface, it is easily removed by wetting, revealing the tacky gel and generating corn starch residue.

As noted above, the best gel materials tend to exhibit surfaces that are very tacky. The use of a tacky gel can make the processes of manufacturing and using gels in seals and access devices extremely difficult. A tacky gel also produces significant drag forces during instrument insertion. Furthermore, the tacky surfaces tend to draw and retain particulate matter during the manufacturing and handling processes. For these reasons it is even more desirable to render the highly tacky gel surfaces non-tacky in the case of medical devices such as access ports and other such devices.

SUMMARY

The present invention is directed to tack-free gels and to methods for manufacturing a tack-free gel pad, comprising the steps of providing a mold; applying a fluorinated ultrahigh molecular weight polyethylene to the mold; heating a gel slurry beyond its curing temperature to a molten state, to thereby produce a molten gel; injecting the molten gel into the mold; and cooling the mold until the gel is set to thereby produce a tack-free gel.

In one embodiment, the mold is textured prior to applying the fluorinated ultrahigh molecular weight polyethylene by spraying the mold with blast media. In another embodiment, the mold is preheated to a temperature of approximately 220° F. to approximately 260° F. prior to applying the fluorinated ultrahigh molecular weight polyethylene. Alternatively, the fluorinated ultrahigh molecular weight polyethylene is applied to the mold by electrostatic coating.

In one embodiment, the fluorinated ultrahigh molecular weight polyethylene comprises a powder having a particle size of approximately 5 μm to approximately 100 μm.

In one embodiment, the mold is preheated to a temperature of approximately 110° F. to approximately 160° F. prior to injecting the molten gel.

In one embodiment, the gel slurry comprises an oil and a elastomer or elastomer. In one embodiment, the gel slurry comprises a ratio by weight of oil to elastomer of approximately 7:1 to 10:1. The oil may comprise a mineral oil and the elastomer may comprise block copolymer styrene-ethylene/butylene-styrene polymer.

In another embodiment of the method, the gel slurry is bulk degassed prior to heating the gel slurry to a molten state. In one embodiment, the gel slurry is bulk degassed at a temperature of approximately 120° F. to approximately 130° F.

An alternative method for making a tack-free gel comprises the steps of: providing a mold; applying a fluorinated ultrahigh molecular weight polyethylene to the mold; preheating the mold to a temperature of approximately 110° F. to approximately 160° F.; heating a gel slurry to a temperature of approximately 125° F.; degassing the gel slurry; dispensing the gel slurry into the mold; degassing the gel slurry a second time; and curing the gel in the mold at a temperature of approximately 140° F. to approximately 160° F. to provide a tack-free gel.

In this embodiment, the gel slurry comprises an oil and an elastomer. The oil may comprise a mineral oil and the elastomer may comprise styrene-ethylene/butylene-styrene polymer. The mold may be textured prior to applying the fluorinated ultrahigh molecular weight polyethylene by spraying the mold with blast media.

The present invention is also directed to surgical access devices adapted to provide access to a cavity in a patient while maintaining a seal between the cavity and an area outside the patient, the access device comprising a gel cap comprising a ring and a gel pad; wherein the ring is configured for alignment with an axis of an access channel defined at least in part by an incision extending through a body wall of a patient, wherein the gel pad is coupled with the ring, disposed substantially within the ring and supported at least partially thereby, the gel pad comprises a mixture of an elastomer and an oil, the gel pad comprises a self-sealing valve and defines at least a portion of an access channel, the self-sealing valve is configured to conform around an object extending through the self-sealing valve and seal the working channel in the absence of an object extending through the self-sealing valve, and wherein a discontinuous layer of polyethylene powder is permanently bonded to an outer surface of the gel pad to thereby create a tack-free surface.

In one embodiment, the polyethylene powder comprises at least one of fluorinated ultrahigh molecular weight polyethylene, unmodified ultrahigh molecular weight polyethylene, oxidized ultrahigh molecular weight polyethylene, high density polyethylene, medium density polyethylene, and low density polyethylene.

In one embodiment, the elastomer comprises at least one of polyurethane, polyvinylchloride, polyisoprene, a thermoset elastomer, a thermoplastic elastomer, a tri-block copolymer, styrene-ethylene/butylene-styrene block copolymer, styrene-isoprene-styrene, styrene-butadiene-styrene, styrene-ethylene/propylene-styrene.

In one embodiment, the oil comprises at least one of mineral oil, vegetable oil, petroleum oil, and silicone oil.

In one embodiment, the gel cap of surgical access device is configured to attach to an adjustable wound retractor.

The present invention is also directed to a method for making a tack-free gel, comprising the steps of providing a polyethylene mold; heating a gel slurry beyond its curing temperature to a molten state, to thereby produce a molten gel; dispensing the molten gel into the mold; and cooling the mold until the gel is set to thereby produce a tack-free gel.

The present invention is also directed to a method for making a tack-free gel, comprising the steps of providing a mold; spraying the mold with a polyethylene spray; heating a gel slurry beyond its curing temperature to a molten state, to thereby produce a molten gel; dispensing the molten gel into the mold; and cooling the mold until the gel is set to thereby produce a tack-free gel.

BRIEF DESCRIPTION OF THE DRAWINGS

FIG. 16 depicts a flow diagram illustrating one process for producing a tack-free gel cap.

DETAILED DESCRIPTION OF CERTAIN EMBODIMENTS

Disclosed herein is a method for producing a tack-free gel. Although described in reference to medical products, and more specifically, to gel pads for use in access systems for laparoscopic surgery, such gels may be used in a wide variety of applications, including non-medical uses, and all such applications are contemplated by this disclosure.

Figure 1:
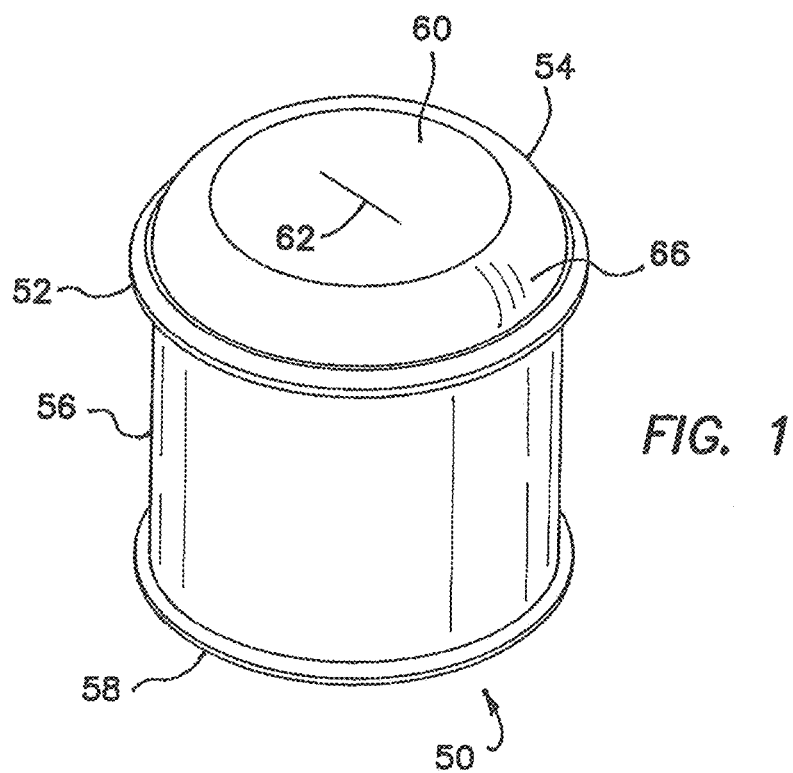
FIG. 1 depicts a top perspective view of an access device of the present invention.
Figure 2:
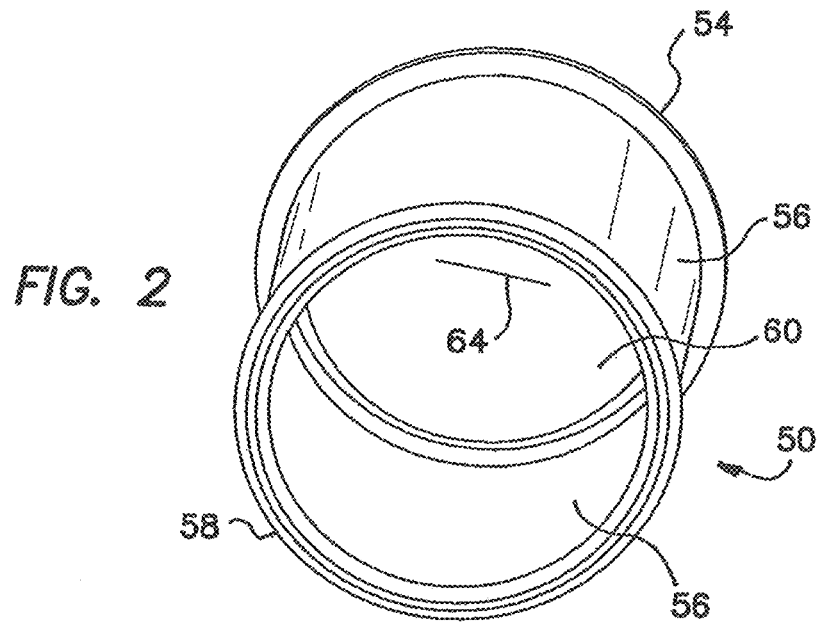
FIG. 2 depicts a bottom perspective view of the access device of FIG. 1.

In FIGS. 1 and 2, a surgical access device 50 according to one aspect of the present invention is shown. The device includes a retainer 52 and a cap 54. The cap 54 and the retainer 52 are both substantially annular and both include an opening therethrough. The retainer 52 is adapted to be placed against a body wall. The retainer 52, in one aspect, is rigid and is associated with and/or capable of being coupled to an elongate sleeve 56. The surgical access device 50 is adapted for disposition relative to an incision in a body wall. The surgical access device 50 also facilitates insertion of an instrument through the access device and maintenance of a sealing relationship with the instrument.

In one aspect, the elongate sleeve 56 extends through an incision to a point where an attached retention ring 58 contacts the interior portions of the body cavity and provides tension between the retainer 52 outside the body cavity and the retention ring. The retainer 52 in one aspect also supports or otherwise enables a portion of the elongate sleeve 56 to remain outside of the body cavity. Additionally, the retainer 52, retention ring 58 and elongate sleeve 56 together allow the incision to be retracted and isolated during a surgical procedure. In one aspect, the elongate sleeve 56 and aspects thereof is a wound retractor type device such as described in U.S. Pat. No. 7,650,887, the disclosure of which is hereby incorporated by reference as if set forth in full herein.

As shown, the retainer 52 and retention ring 58 are circular, but as one skilled in the art would appreciate, they may be of different shapes and sizes. The retainer 52 in one aspect may be either rigid, flexible or a combination of both. The retention ring 58 may be flexible to facilitate insertion into the body cavity. As will be described in more detail, the access device 50 includes coupling means that are adapted for coupling the cap 54 and the retainer 52 together.

A gel pad 60 may be coupled to, attached to, formed or integrated with the cap 54 so that a gas-tight conduit is formed between the cap and the sleeve 56. The gel pad 60 covers and seals the entire opening in the cap 54. In one aspect, the gel pad includes a plurality of intersecting dead-end slits 62, 64 that form an access portion or passage through the gel pad 60. Unlike foam rubber or other similar types of elastic materials, the gel pad 60 provides a gas tight seal around a variety of shapes and sizes of hands or instruments inserted therethrough.

In one aspect, the gel material from which the gel pad 60 is made is an elastomeric gel. Some such gels have been described in U.S. Pat. No. 7,473,221, U.S. Pat. No. 7,481,765, U.S. Pat. No. 7,951,076 and U.S. Pat. No. 8,105,234, the disclosures of which are hereby incorporated by reference as if set forth in full herein. The gel can be prepared by mixing a triblock copolymer with a solvent for the midblocks. The endblocks are typically thermoplastic materials such as styrene and the midblocks are thermoset elastomers such as isoprene or butadiene, e.g., Styrene-Ethylene-Butylene-Styrene (SEBS). In one aspect, the solvent used is mineral oil. Upon heating this mixture or slurry, the midblocks are dissolved into the mineral oil and a network of the insoluble endblocks forms. The resulting network has enhanced elastomeric properties over the parent copolymer. In one aspect, the triblock copolymer used is KRATON G1651, which has a styrene to rubber ratio of 33/67. Once formed, the gel is substantially permanent and, by the nature of the endblocks, processable as thermoplastic elastomers henceforward. The mixture or slurry has a minimum temperature at which it becomes a gel, i.e., the minimum gelling temperature (MGT). This temperature, in one aspect, corresponds to the glass transition temperature of the thermoplastic endblock plus a few degrees. For example, the MGT for the mixture of KRATON G1651 and mineral oil is about 120° C. When the slurry reaches the MGT and the transformation to a gel state takes place, the gel becomes more transparent, thereby providing means for visually confirming when the transformation of the slurry to the gel state is substantially complete and that the gel may be cooled. In addition to triblocks, there are also diblock versions of the materials that may be used where Styrene is present at only one end of the formula, for example, Styrene-Ethylene/Butylene (SEB).

For a given mass of slurry to form into a complete gel, the entire mass of the slurry is heated to the MGT and remains heated at the MGT for sufficient time for the end blocks to form a matrix of interconnections. The slurry will continue to form into gel at temperatures above the MGT until the slurry/gel reaches temperatures at which the components within the slurry/gel begin to decompose or oxidize. For example, when the slurry/gel is heated at temperatures above 250° C., the mineral oil in the slurry/gel will begin to be volatile and oxidize. Oxidizing may cause the gel to turn brown and become oily.

The speed at which a given volume of slurry forms a gel is dependent on the speed with which the entire mass of slurry reaches the MGT. Also, with the application of temperatures higher than the MGT, this speed is further enhanced as the end block networks distribute and form more rapidly.

The various base formulas may also be alloyed with one another to achieve a variety of intermediate properties. For example, KRATON G1701X is a 70% SEB 30% SEBS mixture with an overall Styrene to rubber ratio of 28/72. It can be appreciated that an almost infinite number of combinations, alloys, and Styrene to rubber ratios can be formulated, each capable of providing advantages to a particular embodiment of the invention. These advantages will typically include low durometer, high elongation, and good tear strength.

It is contemplated that the gel material may also include silicone, soft urethanes and even harder plastics that might provide the desired sealing qualities with the addition of a foaming agent. The silicone material may be of the types currently used for electronic encapsulation. The harder plastics may include PVC, Isoprene, KRATON neat, and other KRATON/oil mixtures. In the KRATON/oil mixture, oils such as vegetable oils, petroleum oils and silicone oils may be substituted for the mineral oil.

Any of the gel materials contemplated could be modified to achieve different properties such as enhanced lubricity, appearance, and wound protection. Additives may be incorporated directly into the gel or applied as a surface treatment. Other compounds may be added to the gel to modify its physical properties or to assist in subsequent modification of the surface by providing bonding sites or a surface charge. Additionally, oil based colorants may be added to the slurry to create gels of different colors.

The ratio of mineral oil to KRATON G1651 may be varied depending on the desired gel characteristics and the method of casting the gel pad. In one aspect, the mixture/slurry used with the various embodiments of the caps that are described herein are composed of about 90% by weight of mineral oil and about 10% by weight of KRATON G1651, a nine to one ratio. This is particularly useful in cold cast processes, as described herein. In another aspect, the mixture/slurry are composed of about 89% by weight of mineral oil and about 11% by weight of KRATON G1651, an eight to one ratio. This is preferred for use in hot cast processes, also as described herein. From a thermodynamic standpoint, these mixtures behave similar to mineral oil. Mineral oil has a considerable heat capacity and, therefore, at about 130° C. it can take 3 or 4 hours to heat a pound of the slurry sufficiently to form a homogeneous gel. Once formed, the gel can be cooled as quickly as practical with no apparent deleterious effects on the gel. This cooling, in one aspect, is accomplished with cold-water immersion. In another aspect, the gel may be air-cooled. Those familiar with the art will recognize that other cooling techniques that are well known in the art may be employed and are contemplated as within the scope of the present invention.

Many of the properties of the KRATON/oil mixture will vary with adjustments in the weight ratio of the components. In general, the greater the percentage of mineral oil the less firm the mixture; the greater the percentage of KRATON, the more firm the mixture. If the resultant gel is too soft it can lead to excessive tenting or doming of the gel cap during surgery when a patient's abdominal cavity is insufflated. Excessive tenting or doming may cause the slits 62, 64 to open, providing a leak path. Additionally, if the gel is too soft it might not provide an adequate seal. However, the gel should be sufficiently soft to be comfortable for the surgeon while simultaneously providing good sealing both in the presence of an instrument and in the absence of an instrument.

If the slurry is permitted to sit for a prolonged period of time, the copolymer, such as KRATON, and the solvent, such as mineral oil, may separate. The slurry may be mixed, such as with high shear blades, to make the slurry more homogeneous. However, mixing the slurry may introduce or add air to the slurry. To remove air from the slurry, the slurry may be degassed. In one aspect, the slurry may be degassed in a vacuum, such as within a vacuum chamber. In one aspect, the applied vacuum may be 0.79 meters (29.9 inches) of mercury, or about 1.0 atmosphere. The slurry may be stirred while the slurry is under vacuum to facilitate removal of the air. During degassing within a vacuum, the slurry typically expands, then bubbles, and then reduces in volume. The vacuum may be discontinued when the bubbling substantially ceases. Degassing the slurry in a vacuum chamber reduces the volume of the slurry by about 10%. Degassing the slurry helps reduce the potential of the finished gel to oxidize.

Degassing the slurry tends to make the resultant gel firmer. A degassed slurry composed of about 91.6% by weight of mineral oil and about 8.4% by weight of KRATON G1651, an eleven-to-one ratio, results in a gel having about the same firmness as a gel made from a slurry that is not degassed and that is composed of about 90% by weight of mineral oil and about 10% by weight of KRATON G1651, a nine-to-one ratio.

Mineral oil is of a lighter density than KRATON and the two components will separate after mixing, with the lighter mineral oil rising to the top of the container. This separation may occur when attempting to form static slurry into gel over a period of several hours. The separation can cause the resulting gel to have a higher concentration of mineral oil at the top and a lower concentration at the bottom, e.g., a non-homogeneous gel. The speed of separation is a function of the depth or head height of the slurry being heated. The mass of slurry combined with the head height, the temperature at which the gel sets and the speed with which the energy can be transferred to the gel, factor into the determination or result of homogeneous gel versus a non-homogeneous gel.

The gel pad or gel cap in various aspects of the present invention may be gamma sterilized. The relative or comparative simplicity of qualifying the sterilization process, for example of gamma versus ethylene oxide, of the gel pad and the device with the gel pad is desirable. However, under gamma sterilization large bubbles can form in the gel pad causing potential cosmetic or aesthetic issues in the sterilized devices. The bubbles are more than 99% room air, so removal of the dissolved air in the slurry is performed prior to forming the slurry into gel. For example, the slurry may be degassed via vacuum, as described above, and turned into gel by heat. Bubbles may still form in the gel during gamma sterilization but disappear in a period of about 24 to 72 hours. In one aspect, the percentage of dissolved gas in the mineral oil at room temperature is about 10%. The removal of the air in the gel has an additional effect of making the gel firmer. This however is counterbalanced by the softening effect on the gel caused by gamma radiation during gamma sterilization.

If the gel pad is to be gamma sterilized, the gel may include about 89%-90% mineral oil by weight and about 10%-11% KRATON by weight. As stated above, degassing the slurry has the effect of making the gel firmer. However, the gamma radiation softens the gel to substantially the same firmness as a gel having about 89%-90% mineral oil by weight and about 10%-11% KRATON by weight that is not degassed and gamma sterilized.

In one aspect, cyanoacrylate, e.g., SUPERGLUE or KRAZY GLUE, may be used to bond or otherwise couple or attach the gel pad 60 to the cap 54. The glue may attach to either the rubber or styrene component of the tri-block and the bond is frequently stronger than the gel material itself. In another aspect, a solvent may be used to dissolve the plastics in the cap and the polystyrene in the gel. The solution of solvent is applied to the gel pad and cap in either a spray or dip form. In effect, the solution melts both the plastic of the cap as well as the polystyrene in the gel pad to allow a chemical bond to form between the two, which remains when the solvent evaporates.

Polyethylene can be dissolved in mineral oil and then applied to the gel pad. The mineral oil will not evaporate but will over time absorb into the gel pad and impart a polyethylene layer on the gel pad that may have some beneficial properties.

In one aspect, the gel pad 60 is cast into a DYNAFLEX or KRATON polymer support structure, e.g., the cap 54. By using KRATON polymer or a similar material in the cap, ring adhesion between the gel pad 60 and the cap 54 can be achieved. The polystyrene in the gel is identified as achieving adhesion with polyphenylene oxide (PPO), polystyrene and other polymers.

The cap 54, in one aspect, includes a polymer, e.g., polyethylene (PE). In one aspect, the polyethylene is a low density polyethylene (LDPE) or high density polyethylene (HDPE), or ultrahigh molecular weight polyethylene (UHMWPE). In one aspect, the cap 54 may be made of a polymer, such as polycarbonate and may be fabricated by methods including injection molding.

The gel includes mineral oil. PE has a higher molecular weight than mineral oil. PE is dissolved by mineral oil at high temperatures. As such, as the PE and the mineral oil in the gel pad 60 intermix as both are heated to and held at temperatures above about 130° C., a bond between the PE and gel pad is formed.

In one aspect, the cap 54 includes polycarbonate. The polycarbonate of the cap 54 does not form bonds with the gel pad 60 at 130° C. However, by raising the temperature to about 150° C. for a few minutes during casting, bonding occurs between the gel pad 60 and the cap 54. As such, heating the gel pad 60 and cap 54 to temperatures at which both the polystyrene of the gel and the polycarbonate are simultaneously beyond their melt points allow bonds to form between the gel pad and the cap. Alternatively, the gel pad 60 and cap 54 may be heated to near or at the glass transition temperature of the polycarbonate cap to form the bond between the gel pad and the cap.

Figure 3:
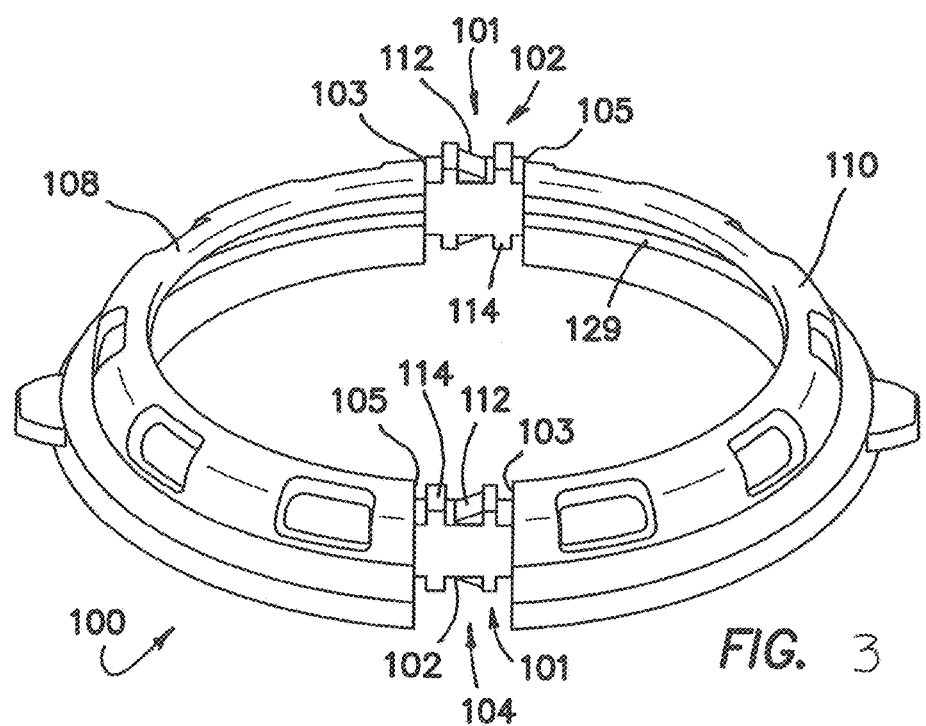
FIG. 3 depicts a top perspective view of a multiple-piece cap having squeeze release buckle connectors molded into the ends of the pieces forming the cap.
Figure 4:
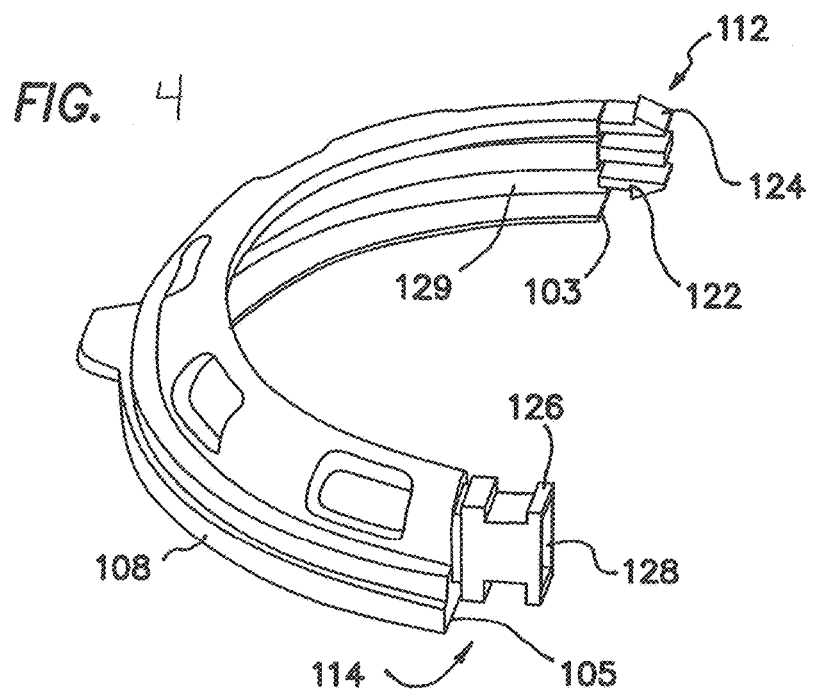
FIG. 4 depicts a top perspective view of one of the pieces of the cap having a male squeeze release buckle connector fitting at one end and a female squeeze release buckle connector fitting at the other end.
Figure 5:
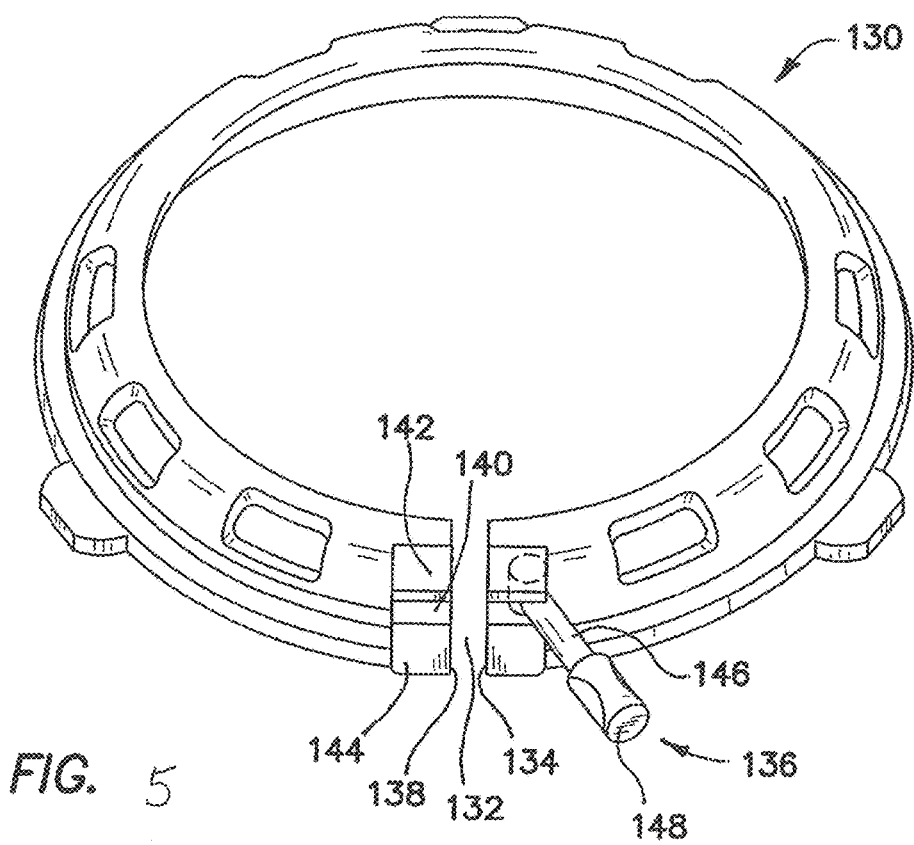
FIG. 5 depicts a top perspective view of a cap having a gap with a latch pivotally coupled on one side of the gap and a groove for accepting the latch on the other side of the gap.

Referring to FIGS. 3-5, the cap 100, 130 includes at least one gap 101, 132 along the annular perimeter of the cap. The at least one gap 101, 132 creates at least one first end 103, 134 and at least one second end 105, 138 of the cap 100, 130. The gap 101, 132 facilitates a transition in the cap from a first, larger periphery to a second, smaller periphery. As will be discussed in more detail below, the cap 100, 130 includes means for maintaining the cap at the second, smaller periphery. When the cap 100, 130 is set at the first, larger periphery, the retainer 52 (FIG. 1) may be inserted into or removed from the opening of the cap. The retainer 52 (FIG. 1) may be fixedly coupled to the cap 100, 130 by transitioning the perimeter of the cap to the second, smaller periphery while the retainer is positioned within the opening of the cap, and maintaining the periphery of the cap at the second, smaller periphery with the maintaining means.

Referring to FIGS. 3-4, the cap 100 incorporates squeeze release buckles 102 molded into or otherwise coupled to the cap. The cap 100 includes a first arc 108 and a second arc 110, the first and second arcs being separated by first and second gaps 101. The first arc 108 has a first barbed portion 112 extending from a first end and adapted to be inserted in a snap fit mating relationship with a second, receiver portion 114 extending from a second end of the second arc 110, thereby coupling the at least one first end 103 of the cap 100 to the at least one second end 105 of the cap. Another barbed portion 112 may extend from the first end of the second arc 110, which is operationally inserted in a snap fit mating relationship with another receiver portion 114 extending from the second end 105 of the first arc 108. In another aspect, the first arc 108 has a barbed portion 112 on each end of the arc with the second arc 110 having corresponding receiver portions 114 on each end of the second arc.

With the first and second arcs 108, 110 placed adjacent to each other, such that the first end 103 of the first arc corresponds with the second end 105 of the second arc and the second end 105 of the first arc corresponds with the first end 103 of the second arc, and prior to being snapped together, the arcs define a first, larger periphery to allow placement of a retainer 52 (FIG. 1) between the two arcs. The barbed portions 112 engage with corresponding receivers 114 coupling the arcs together. Each barbed portion has a plurality of resilient arms 122, two of which have projections 124 extending therefrom. Each receiver 114 has corresponding sidewalls 126 for engaging projections 124 from the barbed portion, which causes the arms 122 to flex towards each other as the arms slide into a channel 128 defined by the receiver. As the projections 124 clear the ends of the sidewalls 126, the arms 122 are allowed to flex away from each other. Engagement or contact between the edges of the projections 124 with edges of the end of the sidewall 126 prevents the arcs 108, 110 from being detached from each other. By coupling the two arcs 108, 110 together, the delimited circumference is reduced to a second, smaller periphery to capture or hold the retainer 52 (FIG. 1). Flexing the arms 122 toward each other allows the barbed portions 112 to disengage from the sidewalls of the corresponding receiver 114 and to slide out from the receiver, thereby allowing the arcs 108, 110 to separate and detach from the retainer 52 (FIG. 1).

Although not shown, additional barbed portions and receiver snap engagements may be included in each arc to assist in the coupling between the cap 100 and the retainer 52 (FIG. 1) or allow for other size and shape configurations of the cap and/or retainer. In one aspect, the cap 100 includes a single gap 101 and a single barbed portion 112 and receiver portion 114 is provided. In one aspect the cap 100 having the single barbed portion 112 and receiver portion 114 may be provided with a hinge or pivot on another portion of the arc.

Referring now to FIG. 5, a cap 130 has a gap or opening 132 along a portion of the periphery of the cap. A latch 136 is hinged or pivotally coupled to the cap proximate a first end 134 of the opening 132 of the cap 130. Proximate a second, opposite end 138 of the opening 132, a latch receiver, such as an aperture or channel 140 defined by substantially parallel channel walls 142, 144, is configured to releasably receive the latch 136. The latch 136 has a shaft 146 coupled to the cap 130 on one end and an enlarged or bulbous head 148 having a perimeter or diameter larger than the perimeter or diameter of the shaft on the non-hinged end of the latch. The head 148 of the latch 136 is configured to be graspable and the latch swung so that the head may engage and be held in the channel 140 defined by the channel walls 142, 144. The width of the channel 140 is smaller than the diameter of the head 148 of the latch 136 and the channel walls 142, 144 are resilient such that the walls flex away from each other during receipt of the head of the latch. Alternatively, or additionally, portions of the head 148 may compress so that the head may be received and held in the channel 140. In one aspect, one or more projections extend from one or both channel walls 142, 144 and engage notches in the head 148, or vice versa, to secure the latch 136 to the channel 140.

In this manner, with the latch 136 open or not engaged with the channel 140, the initial periphery of the cap 130 allows simple placement of the retainer 52 (FIG. 1) within the periphery of the cap. Actuating the latch 136 closes the cap 130 and reduces the size of the periphery delimited by the cap, thereby securing the cap to the retainer 52 (FIG. 1).

Referring back to FIGS. 3-5, with the cap 100, 130 being separable or otherwise disjointed, placement of the respective retainer 52 (FIG. 1) within the inner periphery of the cap is eased. Subsequent joining or recoupling of the cap together secures the retainer and cap to each other. As such, one skilled in the art would recognize that other types of couplings or engagements may be used to couple or join separate portions of the cap and/or the retainer together to close or delimit a periphery to encase or otherwise secure the cap and the retainer together and vice versa. In one aspect, the retainer, or both the retainer and the cap, are separable, having couplings and/or engagements to recouple the separate portions together to secure the cap and retainer to each other.

Figure 6:
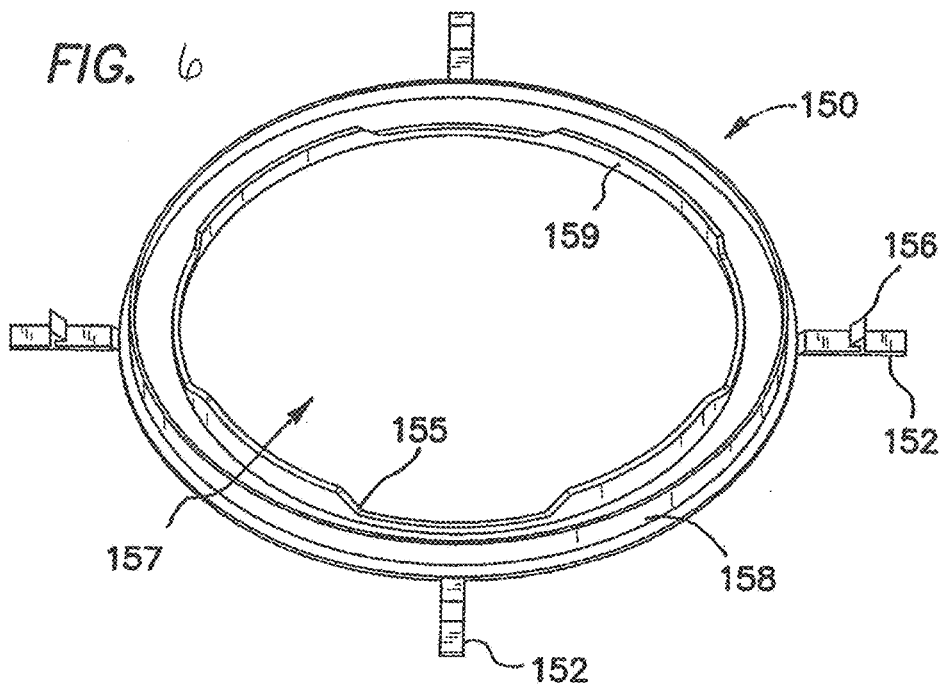
FIG. 6 depicts a top perspective view of a cap having latches for releasable coupling the cap to a retainer.
Figure 7:
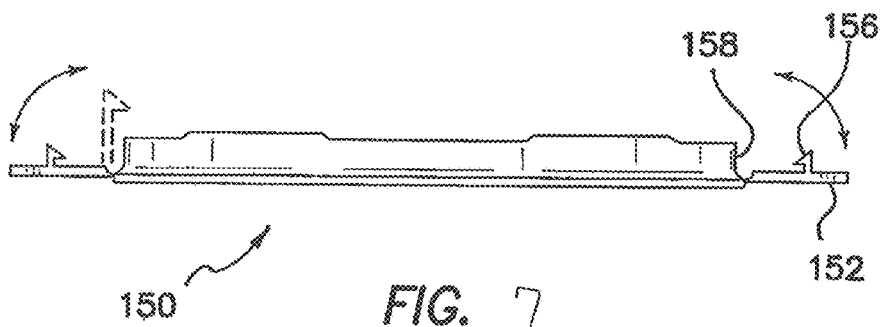
FIG. 7 depicts a side view of the cap of FIG. 6.
Figure 8:
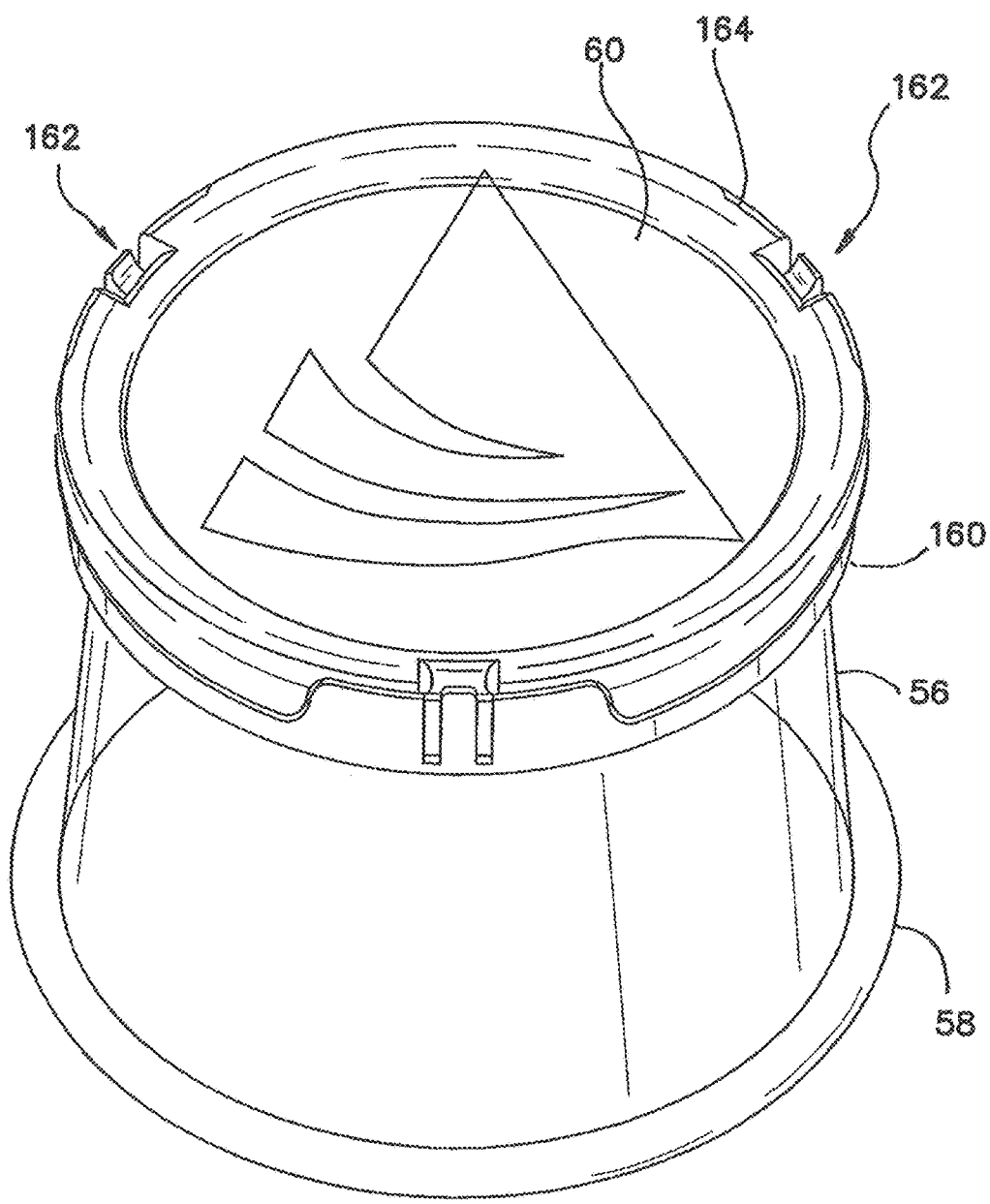
FIG. 8 depicts a top perspective view of an access device of the present invention including a cap and a retainer, the retainer having a plurality of snaps for releasably coupling the retainer to the cap.
Figure 9:
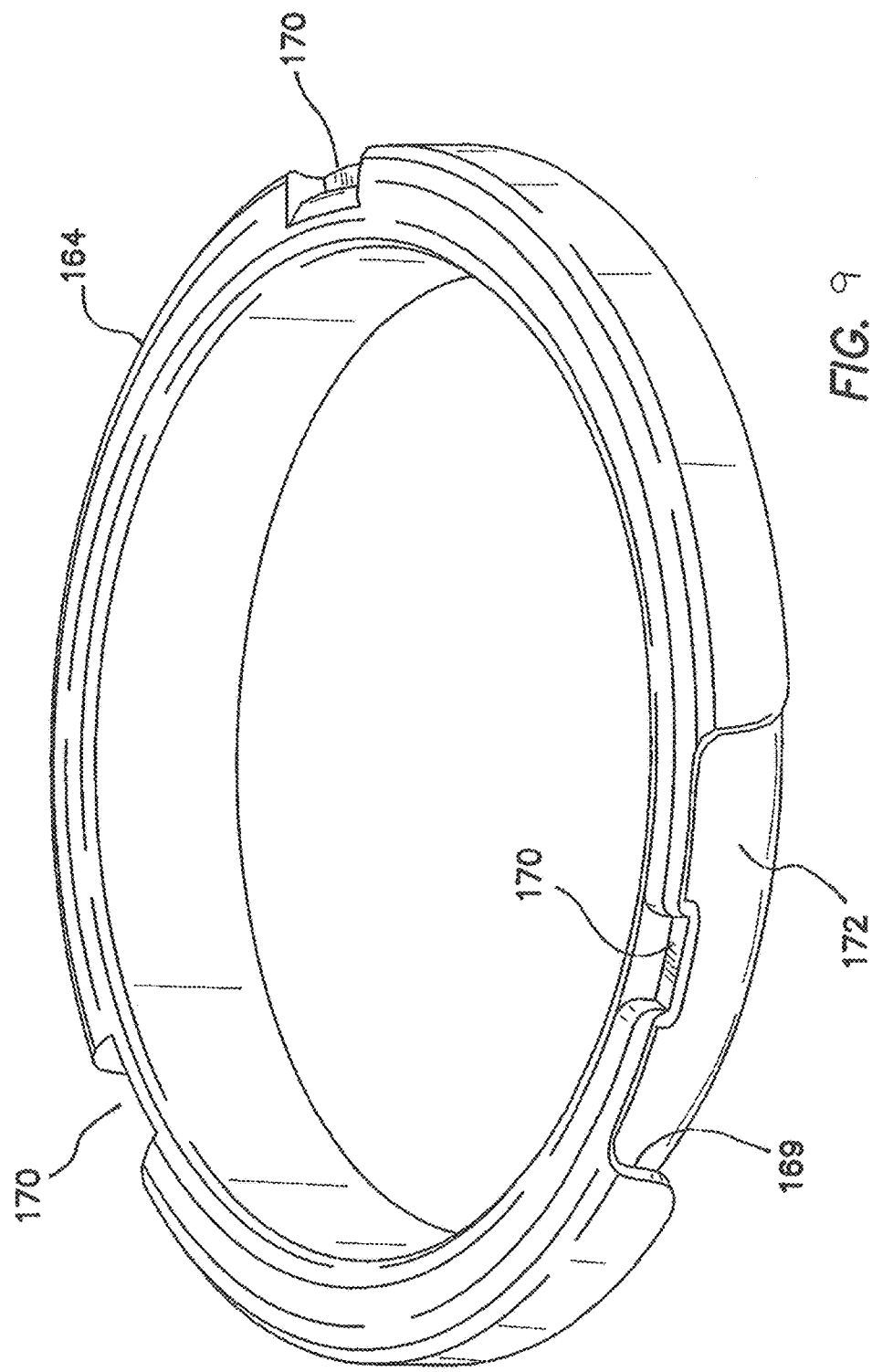
FIG. 9 depicts a top perspective view of the cap of FIG. 8.
Figure 10:
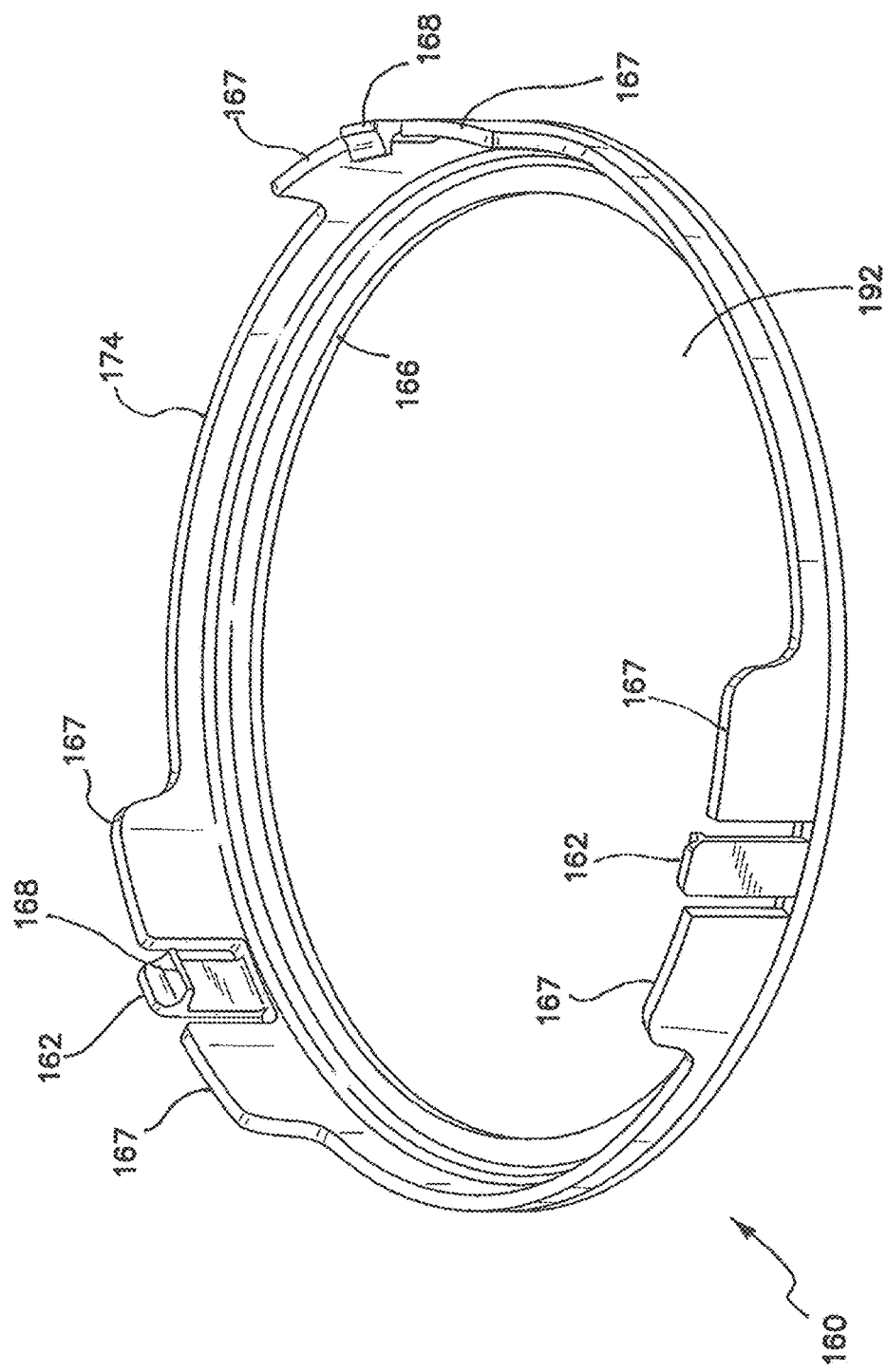
FIG. 10 depicts a top perspective view of the retainer of FIG. 8.
Figure 11:
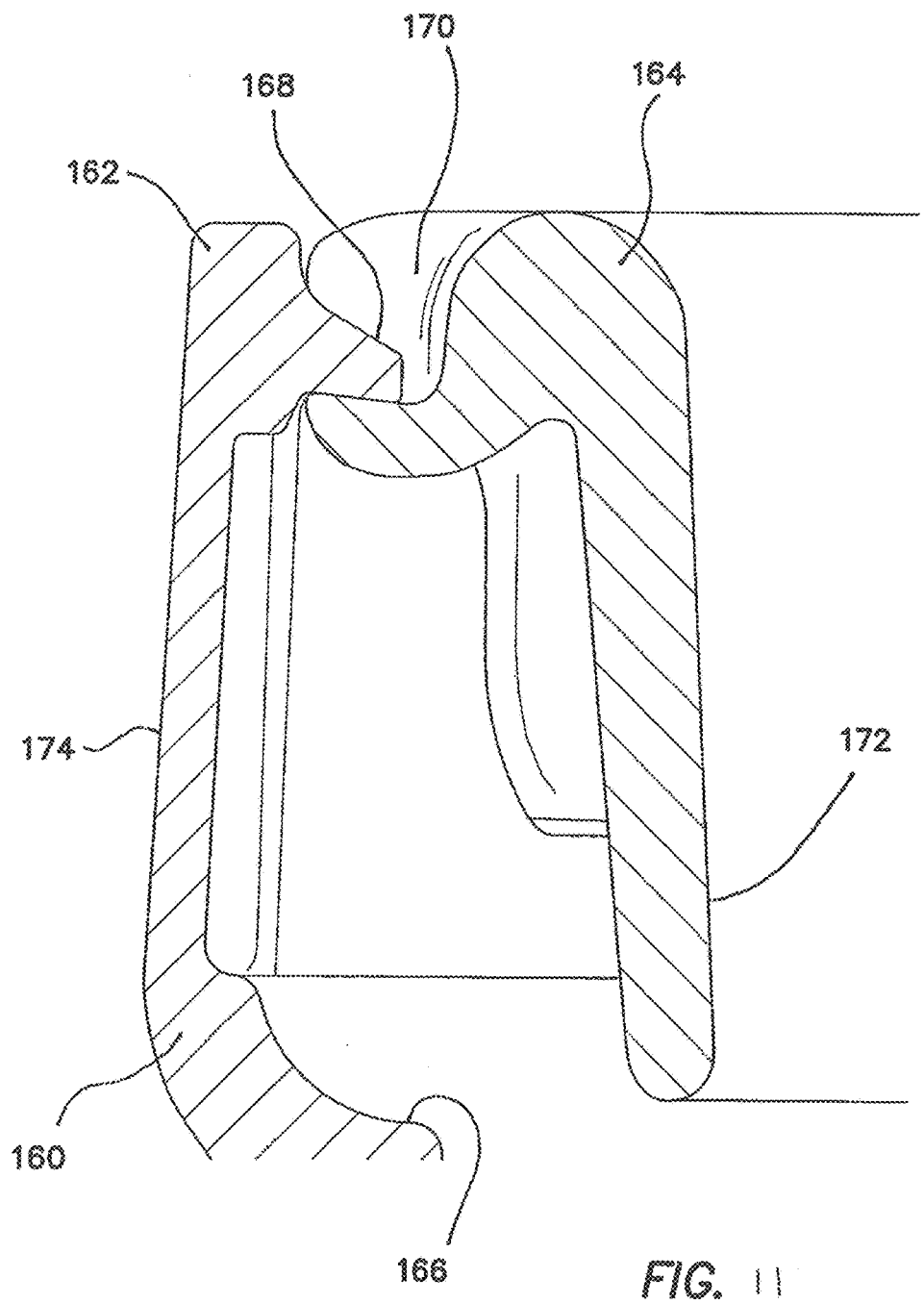
FIG. 11 depicts a section view depicting the interaction between the cap and the retainer of FIG. 8.
Figure 12:
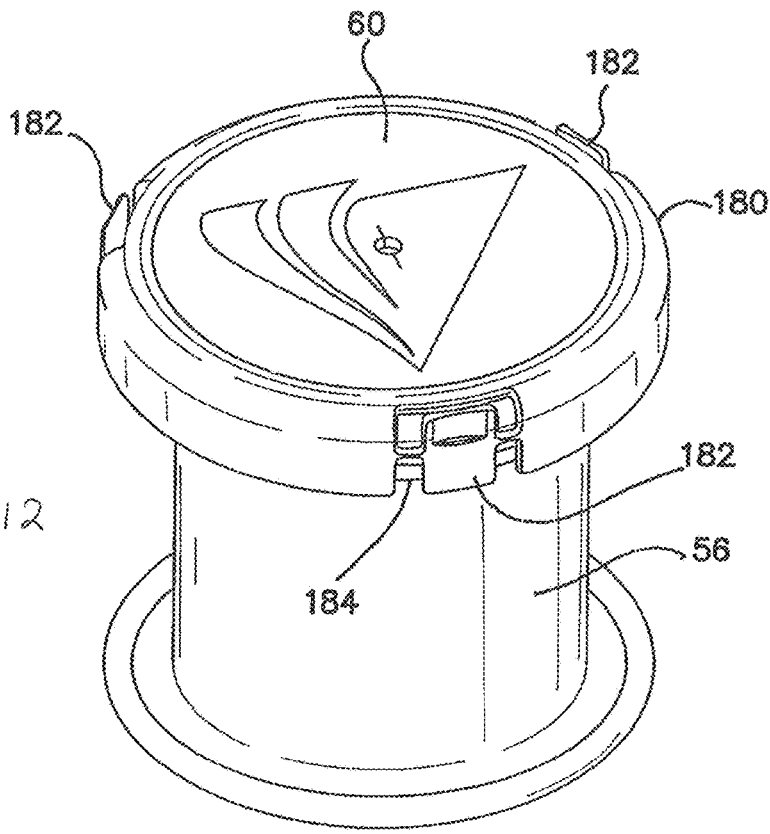
FIG. 12 depicts a top perspective view of an access device of the present invention including a cap and a retainer, the cap having a plurality of snaps for releasably coupling the cap to the retainer.
Figure 13:
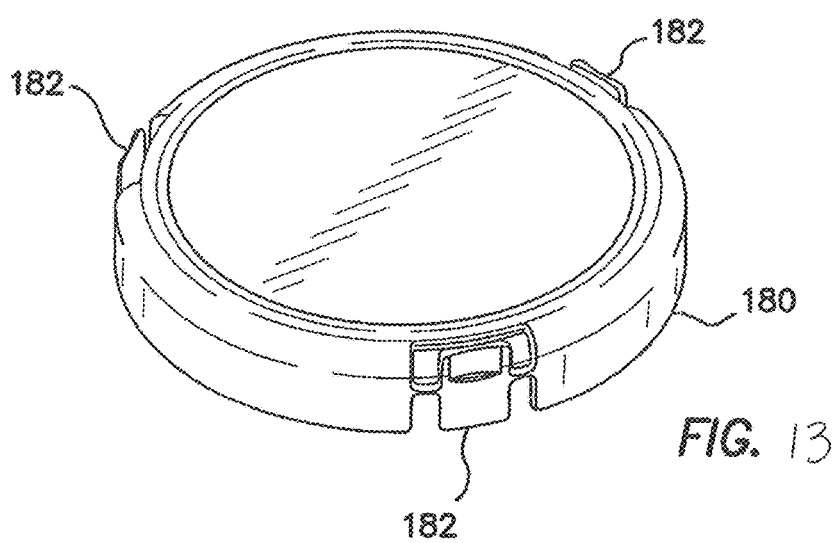
FIG. 13 depicts a top perspective view of the cap of FIG. 12.
Figure 14:
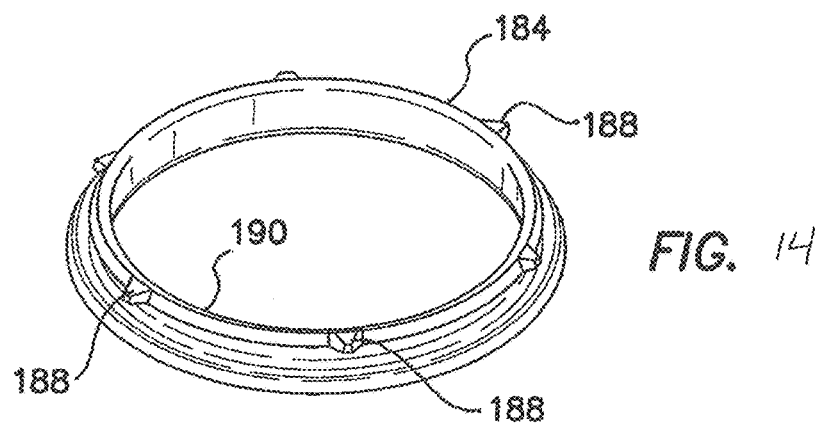
FIG. 14 depicts a top perspective view of the retainer of FIG. 12.
Figure 15:
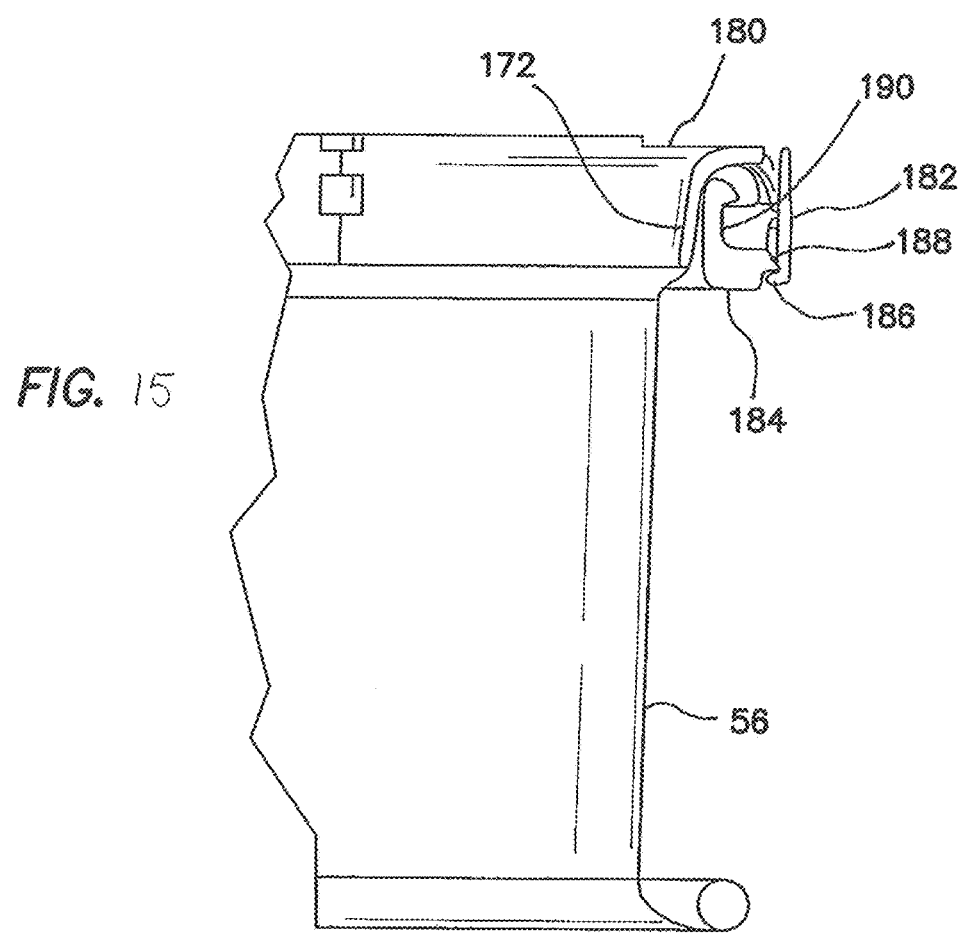
FIG. 15 depicts a section view depicting the interaction between the cap and the retainer of FIG. 12.

In FIGS. 6-7, the retainer 150 has one or more latches 152 to releasably couple the retainer to a cap 54 (FIGS. 1 and 2). In one aspect, a plurality of latches 152 is spaced along the periphery of the retainer 150. The latches 152 are hinged or pivotally coupled to the retainer 150 and are spaced along the periphery of the retainer. In one aspect, each of the latches is coupled to the retainer 150 with a live hinge. In a first position, the latches 152 extend laterally from the periphery of the retainer 150 in a substantially planar relationship with the retainer. Each latch 152 has a projection 156 extending substantially orthogonally from the latch. After placing or fitting the cap 54 on the retainer 150 and/or vice versa, the latches 152 are actuated to couple the cap and retainer together. In particular, the latches 152 are rotated toward the cap to a second position in which the latches engage a portion or edge of the cap 54 to couple the retainer to the cap. In one aspect, the engagement portion of the cap 54 is an opening, aperture, notch, step, projection or other similar type of receiver or engagement to secure the projection of the latch 152 to the cap.

In one aspect, one or more of the latches 152 has notches or openings for receiving corresponding projections or protrusions extending laterally from the cap 54 to couple the retainer 150 to the cap. Additionally or alternatively, although not shown, the cap may have one or more latches hinged along the periphery of the cap for engagement with portions or edges of the retainer to releasably couple the cap and retainer together.

Referring now to FIGS. 8-11, the retainer 160 has one or more resilient snaps 162 for releasably coupling the retainer and a cap 164 together. The snaps 162 extend from the outer periphery or edge of the retainer 160 in a substantially perpendicular direction from a substantially planar, annular surface 166 of the retainer. The planar, annular surface 166 of the retainer 160 secures the sleeve 56 (FIGS. 1 and 2) to the retainer. In one aspect, the surface 166 has projections or hooks to catch and secure the sleeve 56 to the retainer 160 under tension. The edge of the retainer 160 is also slightly raised to assist in the holding of the sleeve 56 and the handling of the retainer.

Multiple snaps 162 may be spaced along the periphery of the retainer 160. In one aspect, portions of the edge of the retainer 160 adjacent to each snap are elevated, thereby forming sidewall portions 167 on either side of each snap. The sidewall portions 167 protect the snaps 162 and strengthen or bolster the coupling between the retainer 160 and the cap 164 once coupled together. Additionally, the sidewall portions 167 facilitate handling and coupling the retainer 160 to the cap 164. Corresponding openings or cutouts 169 are disposed along the edges of the cap 164 to receive the sidewall portions 167 of the retainer 160.

Each snap 162 also has a projection 168 extending substantially perpendicular and radially inwardly from the snap. After placing or fitting a cap 164 on the retainer 160 and/or vice versa, both are squeezed together. The snaps 162 are configured to flex or deflect radially outwardly to slide over a corresponding receiver portion 170, such as a lip portion or an edge, of the cap 164 when the cap and retainer are brought together in a mating relationship. The snaps 162 are also configured to return toward a neutral position after the projection 168 on the snaps pass the receiver portion 170 of the cap 164 such that the projection of the snaps engages the receiver portion 170 of the cap. The receiver portion 170 in one aspect has an opening, aperture, notch, step, projection or other similar type of receiver or engagement means to secure the projection 168 of the snap 162 to the cap 164. Alternatively, one or more of the snaps 162 have notches or openings (not shown) for receiving corresponding projections or protrusions (not shown) extending from the cap to secure the snaps of the retainer 160 to the cap 164. The cap 164 and retainer 160 may each be made via injection molding. Additionally, the cap 164 and retainer 160 may each be made of a polycarbonate material.

In one aspect, as shown in FIGS. 12-15, a cap 180 has one or more snaps 182 for releasably coupling the cap to a retainer 184. The snaps 182 extend perpendicularly from the periphery of the cap 180 for engagement with portions 188, such as corresponding lip portions, and/or edges of the retainer 184. Each snap 182 has a projection 186 extending substantially perpendicular and radially inwardly from the snap. After placing or fitting the cap 180 on the retainer 184, both are squeezed together. The snaps 182 flex or deflect radially outwardly to slide over the lip or edge 188 of the retainer 184 when the cap 180 and retainer are brought together in a mating relationship, thereby securing the cap, retainer and sleeve 56 disposed therebetween. Each snap 182 is configured to return toward a neutral position after the projection 186 on the snap passes the lip portion 188 of the retainer 184 such that the projection of the snap engages the lip portion of the retainer.

Referring now to FIGS. 1-15, the retainers and caps previously described in one aspect are rigid, thereby providing manufacturing benefits as well as easing the assembly of the device. In one aspect, the caps 54, 70, 90, 100, 130, 164, 180 also incorporate an inner cylindrical wall 172 (see FIG. 9) to which the gel pad 60 is bonded or otherwise coupled or attached to the cap. In this manner, the gel pad 60 attaches to a "skeleton" inside the sleeve 56 and provides a sealing area between the device and the wound, incision and/or body cavity. The coupling or intersection of the sleeve, cap and retainer together also provides another sealing area between the device and the body.

By securing the gel pad 60 to the inner cylindrical wall 172, the thickness of the gel pad and corresponding cap 54, 70, 90, 100, 130, 164, 180 is minimized along with the overall footprint of the device. A reduced thickness and overall size of the device provides a lighter device and allows for easier hand or instrument exchanges. With the gel pad thickness reduced and the gel pad being able to be substantially flush or recessed in the cap, the "doming" phenomena produced by gas pressure exerted on the body and device during insufflation is also reduced.

In various aspects (FIGS. 6-15) in accordance with the present invention, the retainer 150, 160 has a raised edge 158, 174 disposed around the outer periphery of the retainer. A raised edge 159, 190, in one aspect, is also disposed around the inner periphery of the retainer 150, 184. The inner periphery defines an opening 157, 192 through which the sleeve extends. The outer raised edge 158, 174 assists in maintaining or securing the releasable coupling between the cap and the retainer. In one aspect, a groove 129 (FIG. 3) extends along the circumference of the cap for receiving the outer raised edge to further enhance the coupling between the cap and retainer. Similarly, the inner raised edge assists in maintaining or securing the releasable coupling between the retainer and the sleeve. The inner raised edge also facilitates the seal between the inner cylindrical wall and/or gel pad, the sleeve and the retainer. In one aspect, notches or spaced valleys or openings 155 (FIG. 6) are disposed along the inner raised edge 159, which facilitates the engagement of the inner cylindrical wall and/or gel pad with the retainer by reducing binding between the components.

Several of the above-described attachments could be modified to integrate the retainer or a retainer like component directly into a sleeve to which the cap is releasably coupled. Similarly, the cap may be integrated directly into the retainer and/or sleeve creating a non-releasable coupling between the components.

In one aspect, casting the gel pad 60 into the cap 54 to form a gel cap 66 includes placing the cap into a mold cavity of a casting mold. The mold cavity may include support for the annular walls of the cap 54. The mold may be made of aluminum, copper, brass, or other mold material having good heat dissipation properties. However, those familiar with the art will recognize that other mold materials having lower heat dissipation properties will produce acceptable parts and these are contemplated as within the scope of the present invention as well.

In another aspect, the gel pad 60 may be molded separately from the cap 54 and coupled to the cap 54 by a secondary operation, such as by bonding. In one aspect, the gel pad 60 may be molded into a gel slug 60 having an outer perimeter smaller than the inner cylindrical wall of the cap 54 and to a height higher that the height of the cap. The gel slug 60 may then be placed within the inner cylindrical wall of the cap 54. The gel slug 60 may be cooled and/or frozen prior to placing it within the inner cylindrical wall of the cap

54. The gel slug 60 may be coupled to the cap 54 through compression molding with the gel slug being compressed longitudinally so that the outer perimeter of the gel slug expands and compresses against the inner cylindrical wall of the cap. The gel slug 60 and cap 54 are heated to a sufficient temperature for the polystyrene of the gel and the polymer of the cap to form bonds between the gel and the cap. Molding the gel slug 60 separately from the cap 54 and heat bonding the gel slug to the cap at a later time is especially useful when the cap is made of a material that has a lower melting temperature than the MGT. In such situations, the gel slug 60 can be molded first and heat bonded to the cap 54 without melting the cap.

Whether molded with the cap or separately, when removed from the mold, the gel pad 60 typically has a tacky surface. In the present invention, the process for manufacturing the gel pad is modified to produce a permanent tack-free coating.

The process integrates powdering and casting steps into one continuous process and permanently bonds a discontinuous layer of fluorinated ultrahigh molecular weight polyethylene (UHMWPE) to the gel pad, creating a tack-free surface. The integration of powdering and casting eliminates the need for secondary powdering and cleaning processes that greatly decreases the amount of time required to touch up gel pads and clean the molds. Using previous processes for manufacturing gel pads, gel remnants are removed from the gel pad, which is then powdered and cleaned of excess oil and powder. The molds of gel that are cast at room temperature and cured in an oven, are left with a sticky residue and require considerable amounts of clean up. Using this new process, the gel is cast hot from an injection molding machine or from an extruder and is free of remnants. Excess powder on the gel pad can be quickly removed using a wipe. Also, pre-powdered molds have no residue and the excess powder left behind in the mold can easily be removed.

The use of polyethylene powder as opposed to starch powder also contributes to process and product improvement. Polyethylene significantly lowers the bioburden of the gel pad as polyethylene is not a growth medium for microorganisms. Further, during the new hot casting process the polyethylene powder is essentially fused onto the surface of the gel, thus eliminating the chance of losing coating residue during gel pad use. In addition, the new process creates a discontinuous coating that doesn't interfere with any of the functional properties of the product or mechanical properties of the material such as sealing and elasticity, respectively. The discontinuous coating allows the gel to be stretched and return to its original form without surface cracking occurring. A continuous coating must have similar elasticity as the gel to prevent cracking or delamination. Materials with high elasticity are generally tacky, the conforming nature of elastomers make it unlikely to have a tack-free surface.

Preferably, gel molds are textured prior to being used in the manufacturing process. Texturing helps stabilize particles on the gel surface by inhibiting particle flow, which would result in uneven particle placement. An abrasive blast cabinet may be utilized to texture the molds. Molds, for example, aluminum molds, are placed inside the cabinet and sprayed with blast media (grit range from about 80 to about 100 grit/mesh) using a pneumatically powered hose until the surface of the mold is uniformly textured. The molds are then removed and sprayed with an air hose to remove excess media.

As an alternative to texturing the molds, the molds may be preheated to a temperature of approximately 240° F. so that the particles adhere more strongly to the smooth surface of the mold. In still another embodiment, charged particles can be held in place during casting by the process of electrostatic coating (e-coating). The electrically conductive molds attract and hold charged particles that are applied to the surface by either spraying or dipping the mold. The e-coating process is robust enough to hold the particles in place until the molten gel is dispensed into the mold.

The molds are powdered with fluorinated UHMWPE prior to adding the gel. In one embodiment, the fluorinated UHMWPE is a powder. In one embodiment, the particle size of the fluorinated UHMWPE powder is approximately 40-50 µm. In another embodiment, the particle size of the fluorinated UHMWPE powder is approximately 45 µm. The particle size of the fluorinated UHMWPE can be varied depending on the desired degree of tackiness. In general, very small particles pack more densely, providing a more tack-free surface, particularly when the underlying gel is stretched.

In other embodiments, other powders than fluorinated UHMWPE can be used to achieve a tack-free surface. Assorted forms of polyethylene powder can be used similarly to the fluorinated UHMWPE. Oxidized UHMWPE essentially provides identical results to that of the fluorinated UHMWPE, the only difference being the method utilized for surface modification of the powder. Also, oxidized UHMWPE may leave a slight residue on the hand after handling gels post radiation sterilization. Other forms of polyethylene powder, such as high density polyethylene (HDPE), medium density polyethylene (MDPE), low density polyethylene (LDPE), and unmodified UHMWPE, can also be employed to achieve the desired tack-free product. However, different powders and their respective particle size provide variable coverage of the tack-free layer. In general, particle sizes ranging from 24 µm to 350 µm may be used to provide gels of varying degrees of tackiness.

In some embodiments, the fluorinated UHMWPE powdered mold is preheated prior to adding the molten gel. Optionally, the powdered mold is preheated with a cap ring or other insert, depending on the final gel product. In one embodiment, the mold is preheated to a temperature range of approximately 110-160° F. The skilled artisan will appreciate that the preheating temperature may vary depending on the thickness of the mold walls and that molds made from very thin walls may not require preheating.

A gel slurry comprising an oil and an elastomer or co-polymer is heated beyond its curing temperature to a molten state and added to the powdered mold. In some embodiments, the oil comprises at least one of mineral oil, vegetable oil, petroleum oil, and silicone oil. In one embodiment, the oil is a mineral oil.

In some embodiments, the elastomer comprises at least one of polyurethane, polyvinylchloride, polyisoprene, a thermoset elastomer, a thermoplastic elastomer, a tri-block copolymer, styrene-ethylene/butylene-styrene block copolymer, styrene-isoprene-styrene, styrene-butadiene-styrene, styrene-ethylene/propylene-styrene. In one embodiment, the elastomer is a block copolymer styrene-ethylene/butylene-styrene polymer. In another embodiment, the elastomer is KRATON G1651.

The ratio by weight of oil to elastomer may vary depending on the desired consistency of the final gel product. For products such as a gel cap useful as an access device in surgery, gel slurries having a ratio by weight of oil to elastomer from approximately 7:1 to approximately 10:1 are useful. In one embodiment, the ratio by weight of oil to elastomer is 8:1.

Because the higher temperatures used to heat the gel slurry to a molten state result in a reduction in molecular weight via oxidative degradation, resulting in a softer durometer gel, a lower ratio of oil to elastomer is generally used than in a cold cast process to compensate for the loss in firmness. By way of example, if a gel is normally produced using a 9:1 ratio by weight of mineral oil to elastomer in a cold-cast process, an 8:1 ratio by weight of mineral oil to elastomer would be used to produce a gel product of similar firmness using the present hot-cast method. As one skilled in the art will appreciate, other ratios may be used to achieve the desired gel characteristics.

In one embodiment, the gel slurry is bulk degassed and pumped into an injection molding machine or an extruder, where it is heated beyond its curing temperature to a molten state. The gel slurry may be degassed at room temperature or at higher temperatures. In one embodiment, the gel slurry is degassed at approximately 125° F.

The molten gel, in one embodiment having a temperature of approximately 460° F. to approximately 480° F., is cast into the mold. If the mold contains a cap or other insert, the gel is cast such that the gel is in contact with the cap/insert.

The powdered mold lid is placed and the unit is cooled to room temperature. The gel cap 66 may be cooled, such as by air-cooling, cold-water immersion, or other cooling means that are well known in the art. At 150° C. the gel pad is soft and if it were distorted during cooling it would set with the distortion included. To reduce the likelihood of distorting the gel pad 60, the gel cap 66 may be cooled within the mold. Cooling times may vary based on parameters including size and configuration of the mold, quantity of gel, temperature and quantity of cooling medium, cooling medium properties and the mold material. As an example, the cooling time may be about two (2) hours if cooling in air and about fifteen (15) minutes if cooling in water. Whether cooling with air or water, the final properties of the gel are substantially the same. The gel cap 66 is typically cooled to about ambient room temperature, but may be cooled to lower temperatures.

The gel cap 66 may be removed from the mold at any time after the gel has set. The powdered molds facilitate demolding as the powder acts as a mold release agent. Accordingly, the gel pad may be removed simply by inverting the mold. The molds are then cleaned and prepared to repeat the process. Using the hot cast process described above, the molten gel is dispensed into the mold as a homogeneous mixture with minimal free oil, eliminating the waxy residue left by cold cast processes after demolding and producing molds that are easier to clean and a consistent tack-free surface on the gel pad. This is significant, because gel slurry batches can vary in the amount of free oil present in the slurry and can lead to difficulties in achieving consistent results. Using a molten gel eliminates this problem.

An overview of the process for producing gel pads having a discontinuous permanent tack-free coating is shown in FIG. 16. In FIG. 16, the gel pad is shown being cast with a cap ring to form a gel cap. However, as one of skill in the art will appreciate, addition of the cap ring is optional for other forms and uses of gel pads. Also, as described above, a cap ring may be added to a gel pad after the gel pad is formed.

Although the preferred process for producing a tack-free gel involves hot casting molten gel, the process can also be used in cold-casting gels. In a cold-cast process, the gel slurry is generally used at a 9:1 ratio by weight of oil to co-polymer. The slurry is heated to approximately 125° F. during degassing before dispensing the degassed slurry into molds, optionally with a cap ring, and degassed a second time prior to curing the gel in the molds at approximately 150° C. for approximately 1.5 hours. The molds can be pre-powdered with fluorinated UHMWPE to provide a tack-free gel, as described above, but because there is more free mineral oil present in the gel slurry, a waxy residue is left behind on the molds after demolding that requires additional cleaning steps before the molds can be reused. Also, gel slurries are more heterogeneous than a molten gel and thus produce a less consistent tack free surface.

In an alternative embodiment of the described methods for producing a tack-free gel, polyethylene molds having varying densities (LDPE, HDPE, for example) can be used in place of traditional metallic molds. In this process, no pre-powdering is required. Gel is cast into the polyethylene mold and cooled to room temperature. Once cool, the gel can be peeled from the mold, with a thin layer of polyethylene transferring to the gel, producing a tack-free surface. Gel can be cast using the above mentioned mold injection method or using a "hot pot" type method. In the "hot pot" method, gel is heated and stirred until molten and poured into a desired cavity. This method may be difficult to control, however, and the molded in stress from the plastic molds sometimes leads to cracks and defects on the tack-free surface. In addition, the high temperatures required to make the gel molten can cause the polyethylene molds to melt or deform and the gel to degrade. As an alternative to the polyethylene mold, a polyethylene insert in a metal mold may be used. The insert is an injection molded polyethylene dish shaped like the desired gel product, which is placed into the mold prior to adding the molten gel. The mold supports the insert and gel. Once the gel is cool, it can be removed from the mold and the insert, leaving a thin layer of polyethylene deposited on the surface of the gel.

Another embodiment utilizes an aerosol polyethylene spray. As with the polyethylene mold process, this method does not require pre-powdering. In this embodiment, molds are sprayed with a polyethylene spray, leaving a thin layer of polyethylene on the surface of the mold. Gel is hot cast into the sprayed molds and cooled to produce a gel product having a residue of polyethylene, leaving behind a tack-free surface. The gel may be cast by either mold injection or the "hot pot" technique. However, it can be difficult to get a uniform coating of polyethylene by spraying the mold surface, producing an uneven distribution of polyethylene on the gel product surface after demolding. A light coating will leave sections of the gel tacky and a heavy coating will lead to cracking of the tack-free layer. Additionally, aerosol sprays release volatile organic compounds (VOCs) to the environment and so are not preferred for manufacturing processes.

Accordingly, the present invention provides a gel having a permanent tack-free coating, methods for making a gel with a permanent tack-free coating and use of such gel in access devices. Although this invention has been described in certain specific embodiments, many additional modifications and variations would be apparent to those skilled in the art. It is therefore to be understood that this invention may be practiced otherwise than specifically described, including various changes in the size, shape and materials, without departing from the scope and spirit of the present invention. Thus, embodiments of the present invention should be considered in all respects as illustrative and not restrictive.

What is claimed is:

1. A method for making a tack-free gel, comprising the steps of:

providing a mold;

applying a fluorinated ultrahigh molecular weight polyethylene to the mold;
heating a gel slurry beyond its curing temperature to a molten state, to thereby produce a molten gel;
injecting the molten gel into the mold; and
cooling the mold until the gel is set to thereby produce a tack-free gel.

2. The method of claim 1, wherein the mold is textured prior to applying the fluorinated ultrahigh molecular weight polyethylene by spraying the mold with blast media.

3. The method of claim 1, wherein the mold is preheated to a temperature of approximately 220° F. to approximately 260° F. prior to applying the fluorinated ultrahigh molecular weight polyethylene.

4. The method of claim 1, wherein the fluorinated ultrahigh molecular weight polyethylene is applied to the mold by electrostatic coating.

5. The method of claim 1, wherein the fluorinated ultrahigh molecular weight polyethylene comprises a powder having a particle size of approximately 5 μm to approximately 100 μm.

6. The method of claim 1, wherein the mold is preheated to a temperature of approximately 110° F. to approximately 160° F. prior to injecting the molten gel.

7. The method of claim 1, wherein the gel slurry comprises an oil and an elastomer.

8. The method of claim 7, wherein the gel slurry comprises a ratio by weight of oil to elastomer from approximately 7:1 to approximately 10:1.

9. The method of claim 7, wherein the oil comprises a mineral oil and the elastomer comprises block copolymer styrene-ethylene/butylene-styrene polymer.

10. The method of claim 1, wherein the gel slurry is bulk degassed prior to heating the gel slurry to a molten state.

11. The method of claim 10, wherein the gel slurry is bulk degassed at a temperature of approximately 120° F. to approximately 130° F.

12. A method for making a tack-free gel, comprising the steps of:
providing a mold;
applying a fluorinated ultrahigh molecular weight polyethylene to the mold;
preheating the mold to a temperature of approximately 110° F. to approximately 160° F.;
heating a gel slurry to a temperature of approximately 125° F.;
degassing the gel slurry;
dispensing the gel slurry into the mold;
degassing the gel slurry a second time; and
curing the gel in the mold at a temperature of approximately 140° F. to approximately 160° F. to provide a tack-free gel.

13. The method of claim 12, wherein the mold is textured prior to applying the fluorinated ultrahigh molecular weight polyethylene by spraying the mold with blast media.

14. The method of claim 12, wherein the gel slurry comprises an oil and an elastomer.

15. The method of claim 14, wherein the oil comprises a mineral oil and the elastomer comprises styrene-ethylene/butylene-styrene polymer.

16. A method for making a tack-free gel, comprising the steps of:
providing a mold;
spraying the mold with a polyethylene spray;
heating a gel slurry beyond its curing temperature to a molten state, to thereby produce a molten gel;
dispensing the molten gel into the mold; and
cooling the mold until the gel is set to thereby produce a tack-free gel.

* * * * *